(12) United States Patent
Jacobs et al.

(10) Patent No.: US 11,071,547 B2
(45) Date of Patent: Jul. 27, 2021

(54) ABDOMINAL CLOSURE METHOD AND DEVICE FOR VENTRAL HERNIA

(71) Applicant: Absolutions Med, Inc., Mountain View, CA (US)

(72) Inventors: Daniel Jacobs, Mountain View, CA (US); Gregory Lamps, Smyrna, GA (US); Christopher Scott Jones, Menlo Park, CA (US); Leigh Boros, Marietta, GA (US); Brad Richardson, Mountain View, CA (US); Frederick Mark Payne, Palo Alto, CA (US)

(73) Assignee: Absolutions Med, Inc., Mountain View, CA (US)

(*) Notice: Subject to any disclaimer, the term of this patent is extended or adjusted under 35 U.S.C. 154(b) by 217 days.

(21) Appl. No.: 16/565,097

(22) Filed: Sep. 9, 2019

(65) Prior Publication Data
US 2020/0078018 A1    Mar. 12, 2020

Related U.S. Application Data

(60) Provisional application No. 62/730,163, filed on Sep. 12, 2018, provisional application No. 62/867,730, filed on Jun. 27, 2019.

(51) Int. Cl.
*A61B 17/08* (2006.01)
*A61B 17/00* (2006.01)

(52) U.S. Cl.
CPC .... *A61B 17/08* (2013.01); *A61B 2017/00654* (2013.01); *A61B 2017/081* (2013.01)

(58) Field of Classification Search
CPC .............. A61B 17/08; A61B 2017/081; A61B 2017/088
See application file for complete search history.

(56) References Cited

U.S. PATENT DOCUMENTS

| 363,538 A | 5/1887 | Penny |
|---|---|---|
| 3,698,395 A | 10/1972 | Hasson |

(Continued)

FOREIGN PATENT DOCUMENTS

| CN | 204428091 U | 7/2015 |
|---|---|---|
| CN | 106901789 | 6/2017 |

(Continued)

OTHER PUBLICATIONS

Fernandez, L., "Abdominal Closure," *Medscape*, https://emedicine.medscape.com/article/1961789-technique, Jun. 14, 2019.

(Continued)

*Primary Examiner* — Wade Miles
(74) *Attorney, Agent, or Firm* — Levine Bagade Han LLP

(57) ABSTRACT

An abdominal closure method and device is disclosed where the device generally includes a first tissue securement member configured for securement to a first tissue region and a second tissue securement member configured for securement to a second tissue region. The first and second tissue securement members are coupled to the connecting member and the connecting member is positionable at a distance from the first and second tissue regions. Additionally, one or more biasing elements may be connected to the first and second tissue securement members to approximate the first and second tissue regions towards one another via respective securement members.

42 Claims, 26 Drawing Sheets

(56) References Cited

U.S. PATENT DOCUMENTS

| | | |
|---|---|---|
| 3,926,193 A | 12/1975 | Hasson |
| 3,986,493 A | 10/1976 | Hendren |
| 4,060,089 A | 11/1977 | Noiles |
| 4,430,998 A | 2/1984 | Harvey et al. |
| 4,539,990 A | 9/1985 | Stivala |
| 4,548,202 A | 10/1985 | Duncan |
| 4,610,250 A | 9/1986 | Green |
| 4,667,674 A | 5/1987 | Korthoff et al. |
| 4,805,617 A | 2/1989 | Bedi et al. |
| 4,950,284 A | 8/1990 | Green et al. |
| 5,234,462 A | 8/1993 | Pavletic |
| 5,258,012 A | 11/1993 | Luscombe et al. |
| 5,263,971 A | 11/1993 | Hirshowitz et al. |
| 5,293,881 A | 3/1994 | Green et al. |
| 5,358,510 A | 10/1994 | Luscombe et al. |
| 5,534,010 A | 7/1996 | Peterson |
| 5,662,649 A | 9/1997 | Huebner |
| 5,916,224 A | 6/1999 | Esplin |
| 6,485,503 B2 | 11/2002 | Jacobs et al. |
| 6,645,226 B1 | 11/2003 | Jacobs et al. |
| 6,730,014 B2 | 5/2004 | Wilk |
| 6,893,452 B2 | 5/2005 | Jacobs |
| 6,991,643 B2 | 1/2006 | Saadat |
| 7,156,862 B2 | 1/2007 | Jacobs et al. |
| 7,172,615 B2 | 2/2007 | Morriss et al. |
| 7,361,185 B2 | 4/2008 | O'Malley et al. |
| 7,445,010 B2 | 11/2008 | Kugler et al. |
| 7,510,566 B2 | 3/2009 | Jacobs et al. |
| 7,972,347 B2 | 7/2011 | Garvin et al. |
| 8,114,101 B2 | 2/2012 | Criscuolo et al. |
| 8,323,313 B1 | 12/2012 | Belson et al. |
| 8,663,275 B2 | 3/2014 | O'Malley et al. |
| 8,764,778 B2 | 7/2014 | Yeretsian |
| 8,801,754 B2 | 8/2014 | Walshe |
| 8,915,942 B2 | 12/2014 | Zhang |
| 9,179,914 B2 | 11/2015 | Belson et al. |
| 9,198,689 B2 | 12/2015 | Dale et al. |
| 9,271,730 B2 | 3/2016 | Fleischmann |
| 9,414,840 B2 | 8/2016 | Fleischmann |
| 9,474,529 B2 | 10/2016 | Belson et al. |
| 9,486,217 B2 | 11/2016 | Moustafa |
| 9,554,799 B2 | 1/2017 | Belson et al. |
| 9,662,112 B2 | 5/2017 | Nash et al. |
| 9,693,776 B1 | 7/2017 | Moustafa |
| 10,010,710 B2 | 7/2018 | Belson et al. |
| 10,022,216 B2 | 7/2018 | Ricci et al. |
| 10,456,136 B2 | 10/2019 | Belson et al. |
| 2004/0059358 A1 | 3/2004 | Kortenbach et al. |
| 2004/0138683 A1 | 7/2004 | Shelton et al. |
| 2004/0267309 A1 | 12/2004 | Garvin |
| 2005/0197699 A1 | 9/2005 | Jacobs et al. |
| 2006/0074448 A1 | 4/2006 | Harrison et al. |
| 2006/0167482 A1 | 7/2006 | Swain et al. |
| 2006/0247637 A1 | 11/2006 | Colleran et al. |
| 2008/0046008 A1 | 2/2008 | Smith et al. |
| 2008/0262540 A1 | 10/2008 | Bangera et al. |
| 2008/0262543 A1 | 10/2008 | Bangera et al. |
| 2009/0163937 A1 | 6/2009 | Kassab et al. |
| 2009/0234358 A1 | 9/2009 | Morales et al. |
| 2011/0092993 A1 | 4/2011 | Jacobs |
| 2012/0029539 A1 | 2/2012 | Dennis |
| 2012/0130374 A1 | 5/2012 | Bouduban et al. |
| 2012/0221044 A1 | 8/2012 | Archibald et al. |
| 2013/0325046 A1 | 12/2013 | Terwiske et al. |
| 2014/0094830 A1 | 4/2014 | Sargeant et al. |
| 2014/0214078 A1 | 7/2014 | Moustafa |
| 2014/0316323 A1 | 10/2014 | Kanevsky et al. |
| 2016/0095591 A1 | 4/2016 | Smith et al. |
| 2016/0113650 A1 | 4/2016 | Lord et al. |
| 2016/0310140 A1 | 10/2016 | Belson et al. |
| 2017/0156847 A1 | 6/2017 | Ricci et al. |
| 2018/0078257 A1 | 3/2018 | Buttar |
| 2018/0214148 A1 | 8/2018 | Christiansen et al. |
| 2019/0038274 A1 | 2/2019 | Quintero et al. |
| 2019/0167260 A1 | 6/2019 | Levinson et al. |
| 2020/0107826 A1 | 4/2020 | Kojouri et al. |
| 2020/0323614 A1 | 10/2020 | Lamps et al. |

FOREIGN PATENT DOCUMENTS

| | | |
|---|---|---|
| CN | 107822682 | 3/2018 |
| WO | WO 2017/000758 | 1/2017 |
| WO | WO 2018/031509 | 2/2018 |
| WO | WO 2018/069543 | 4/2018 |
| WO | WO 2020/055757 | 3/2020 |
| WO | WO 2020/072259 | 4/2020 |
| WO | WO 2020/210463 | 10/2020 |

OTHER PUBLICATIONS

Lorenz® Plating System LactoSorb® RapidFlap™ LS brochure, 4 pages, Oct. 1, 2008.

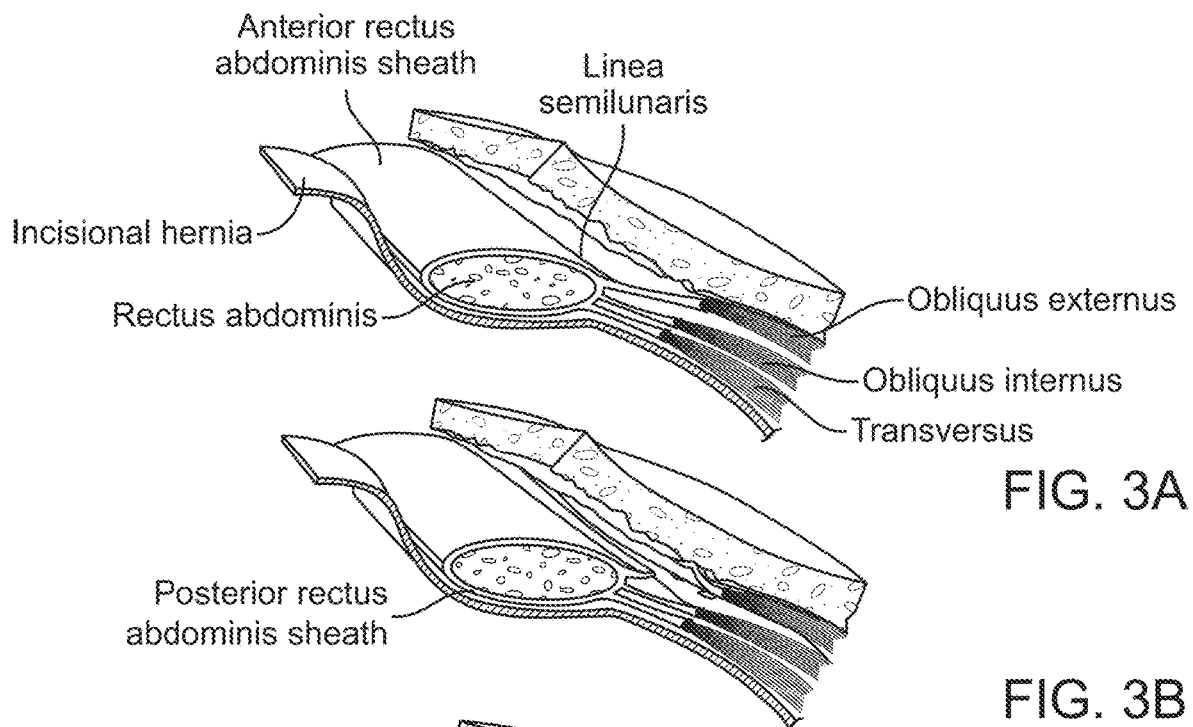
FIG. 3A
FIG. 3B
FIG. 3C
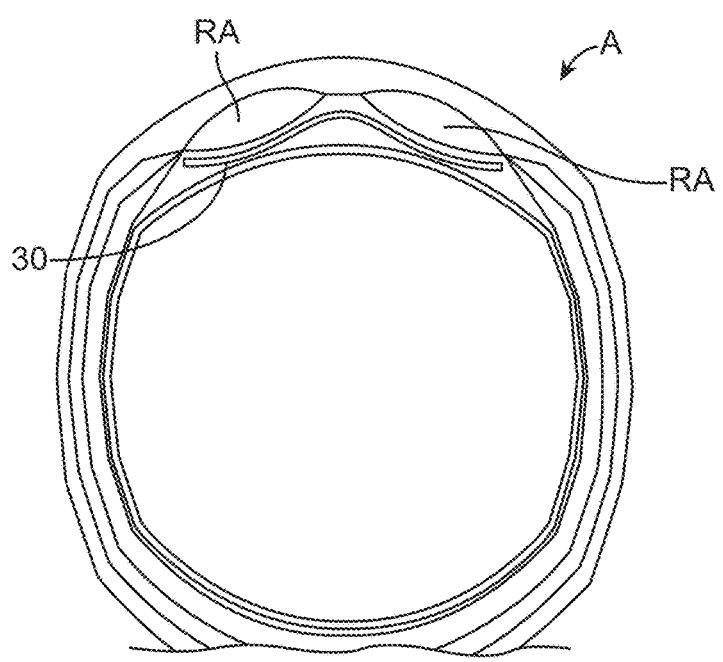
FIG. 4

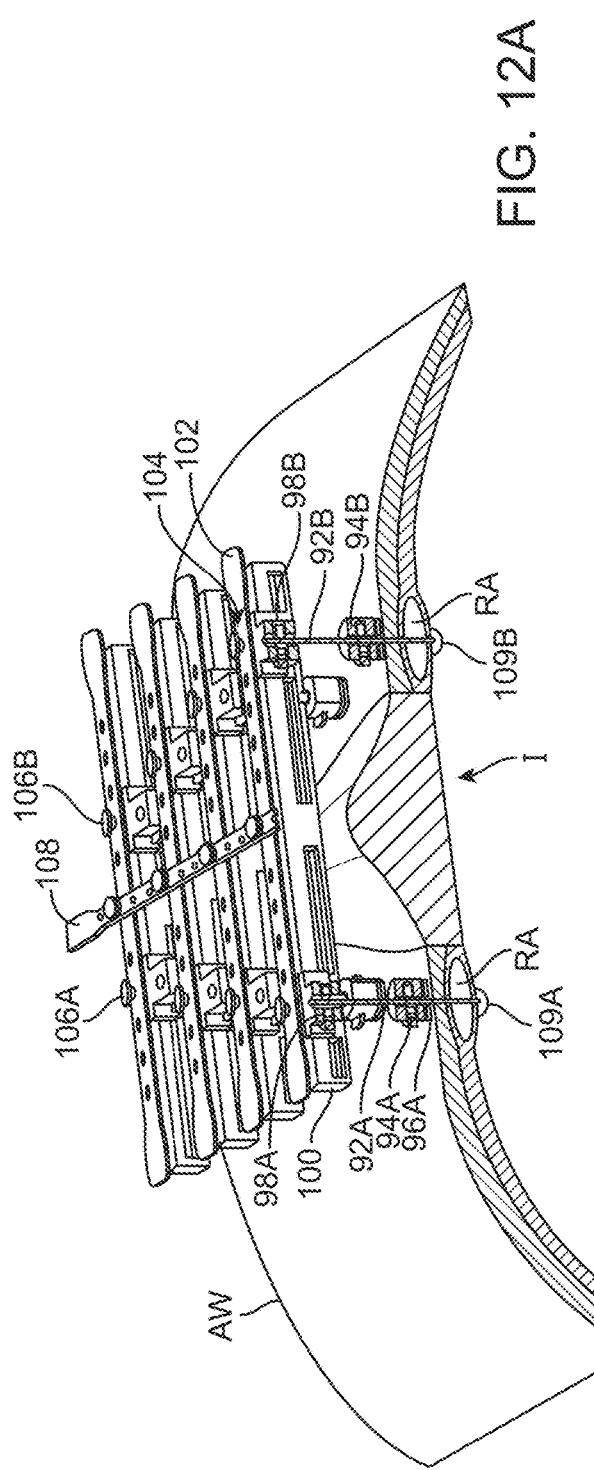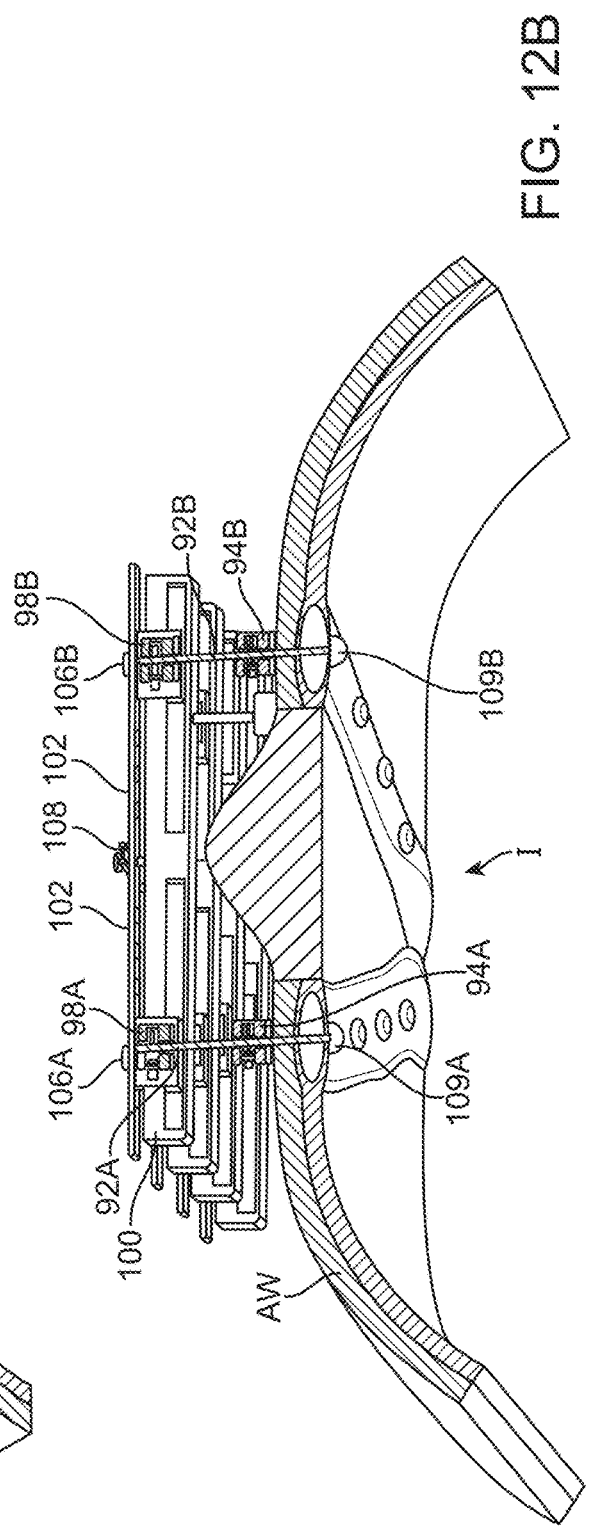

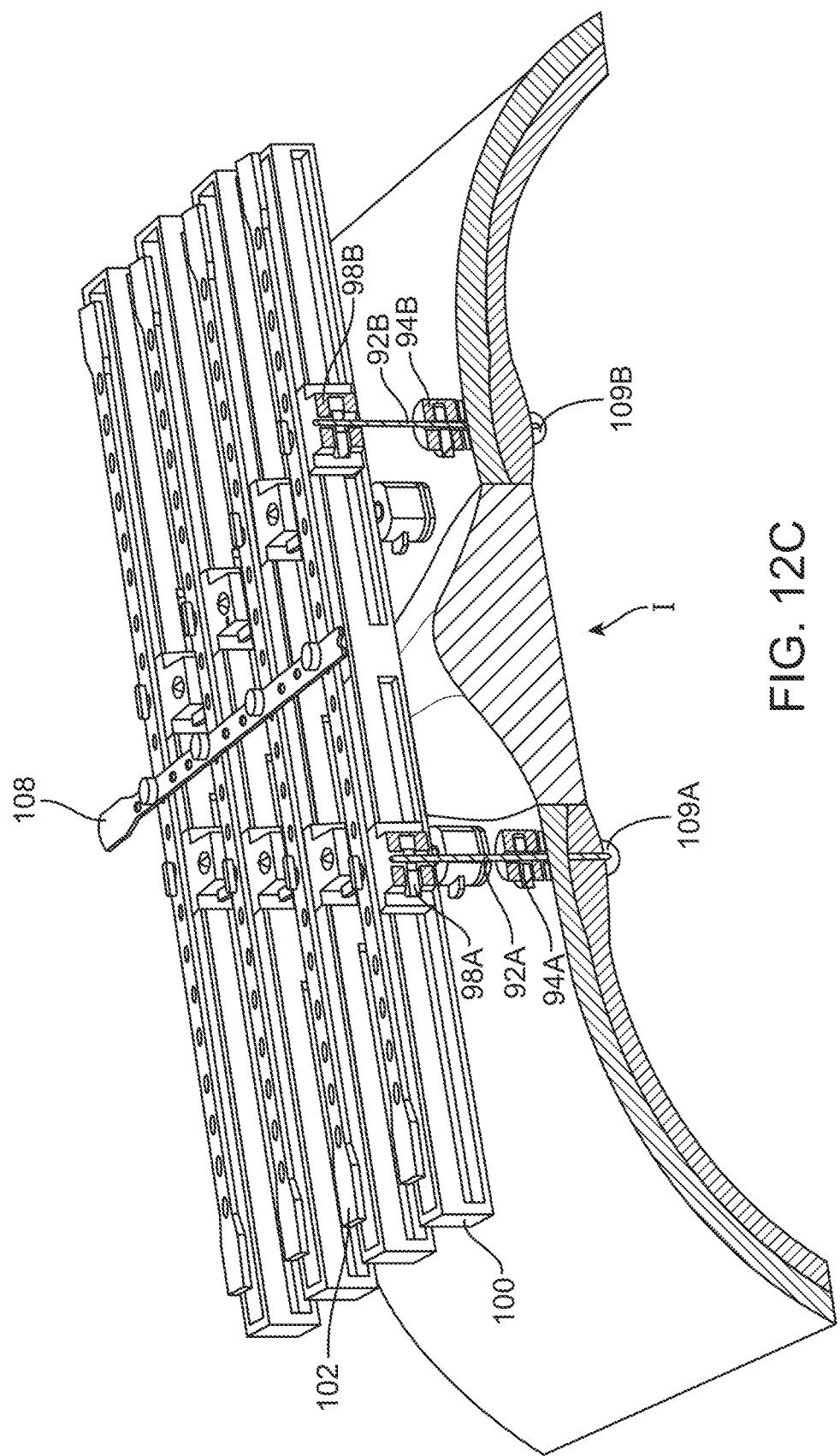

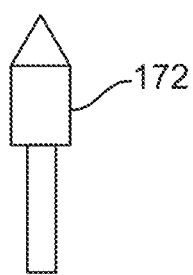
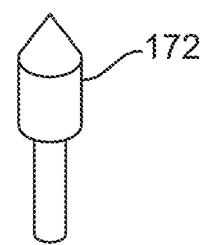
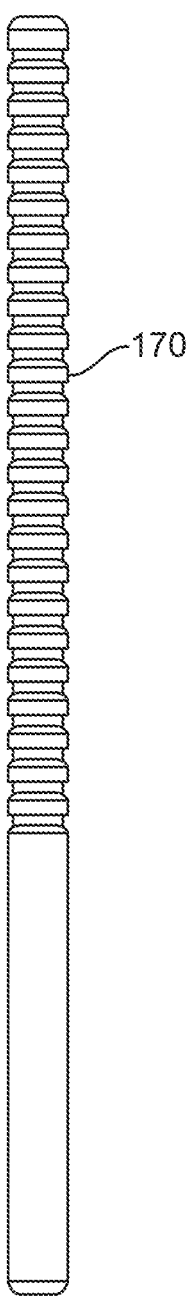
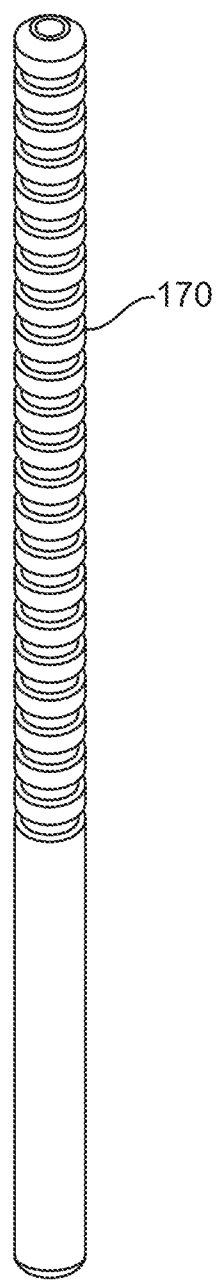
FIG. 21A    FIG. 21B

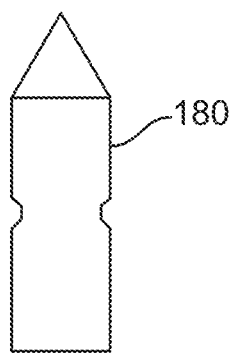
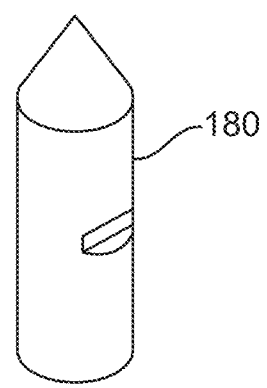
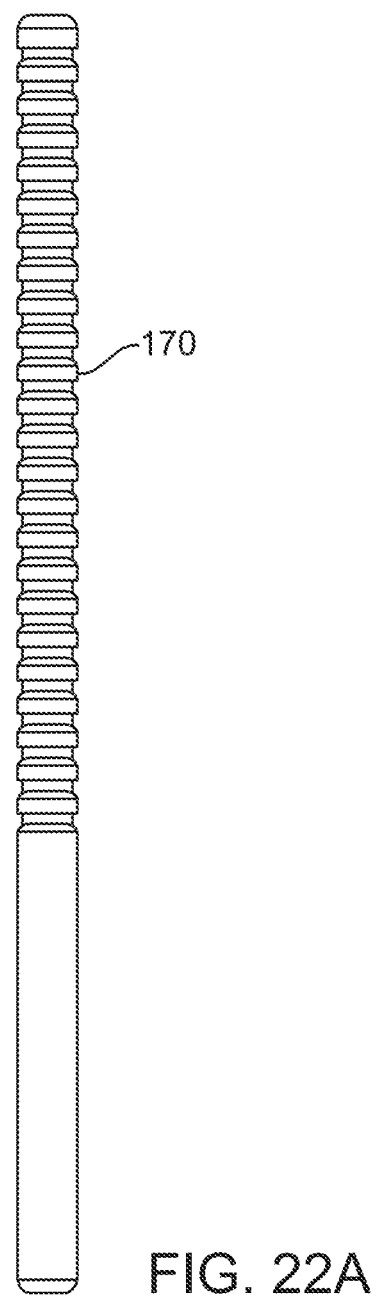
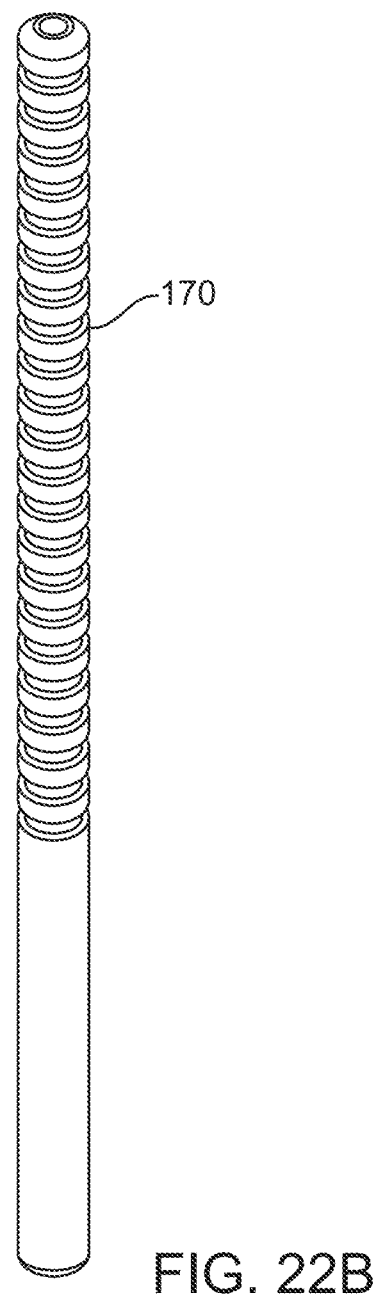
FIG. 22A     FIG. 22B

ABDOMINAL CLOSURE METHOD AND DEVICE FOR VENTRAL HERNIA

CROSS-REFERENCE TO RELATED APPLICATIONS

This application claims the benefit of priority to U.S. Prov. App. 62/730,163 filed Sep. 12, 2018 and 62/867,730 filed Jun. 27, 2019, each of which is incorporated herein by reference in its entirety.

FIELD OF THE INVENTION

The present invention relates to methods and apparatus for approximating tissue regions. More particularly, the present invention relates to methods and apparatus for approximating edges of a wound towards one another while maintaining a distance of the apparatus from the wound so that contact with the wound itself and potentially neighboring vital structures is inhibited.

BACKGROUND OF THE INVENTION

A ventral hernia occurs when there is a defect in the fascia and/or muscles of the anterior abdominal wall. Defects or comprised abdominal walls most commonly result from prior fascial incisions that did not adequately heal (incisional hernia), but also result from pregnancy, and de novo.

There are an estimated four million open abdominal surgeries in the United States and a commonly documented postoperative complication is incisional hernia, which occurs in up to 20% of patients after attempted abdominal closure. FIG. 1 shows an abdomen A of a patient illustrating common sites for ventral hernias, e.g., epigastric, abdominal, and incisional hernias.

Treatments for ventral hernias can fall into three typical categories: (1) spanning the defect with a prosthetic or biologic patch (e.g., mesh), (2) closing the defect under some tension and supporting the closure with a prosthetic or biologic patch, and (3) abdominal wall component separation in which a layer or layers of the muscles and fascia of the abdominal wall are divided in order to allow components to advance towards the midline such that the defect is closed with no abdominal wall gap—also usually supported by a patch. All techniques have profound drawbacks, much of which are associated with the use of a patch.

Mesh used to span abdominal wall defects or to support a fascial closure is a foreign body, fraught with all of the inherent risks that foreign bodies impose. The two most significant risks in this setting are infection and erosion into critical structures such as bowel. Both are devastating events. In the event of infection, whether acute or delayed, removing the mesh from the tissue that has grown into its interstices can be surgically traumatic if not impossible. Erosion into bowel not only sets infection into play, but additionally creates a life threatening or quality-of-life destroying loss of intestinal integrity, with intestinal contents leaking freely into the abdominal cavity, mesh, or through holes in the skin (enterocutaneous fistula). FIG. 2 shows an example of mesh 10 that has eroded into surrounding intestinal tissue.

Abdominal wall component separation is not only a lengthy and involved surgical procedure, but inherently weakens and compromises function of the abdominal wall. It typically also utilizes mesh to support the fascial closure, thus suffering from the risks inherent in such a foreign body such as infection, erosion, and failure. An example of abdominal wall component separation is illustrated in the detail cross-sectional views of FIGS. 3A to 3C and an example of a surgical mesh 30 placed in the retrorectus plane in support of a midline closure is illustrated in the partial cross-sectional view of FIG. 4.

An additional situation that abdominal surgeons often encounter is that of the difficult abdominal closure after trauma or extensive abdominal surgery. In such situations, swelling of the abdominal contents increases the intra-abdominal volume such that closure of the abdominal wall is either impossible or performed under excessively high tension. Soft tissues, however, cannot tolerate high tensions, and typically fail to remain apposed through healing, thus leading to a ventral hernia. Surgeons often use large retention sutures to hold the abdominal wall in position during the early post-operative phases in an attempt to prevent dehiscence (separation). Examples are shown in FIG. 5 which illustrates retention sutures with backing components 40 placed on both sides of the incision I and in FIG. 6 which illustrates retention sutures 50 directly across the midline of the incision I along the abdomen A.

Retention sutures 50, by design, typically have a segment running across the midline of the incisional closure both above and below (deep to) the abdominal wall AW, as shown in the schematic cross-sectional detail view of FIG. 7. The sutures 50 are placed such that a potential trapping space is defined between the suture 50 and the posterior abdominal wall; vector arrows 54 illustrate the net direction of force at the turning points of the suture 50 in the posterior fascia and skin. The segment below (deep to) the abdominal wall poses a threat to underlying bowel tissue. In addition, retention sutures 50, like most sutures, are relatively rigid and sharp, and can cut through tissue leading to incisional separation and failure of the repair. The length of suture placed against the skin surface may be enclosed in a tubular member 52 to prevent or inhibit erosion into the skin.

One approach to the difficult to close abdomen is the ABRA® Abdominal Wall Closure System 60 (Canica Design, Inc., Ontario, Canada) which entails multiple elastic members 62 crossing an open wound and applying tension that can be adjusted regularly by the surgeon in order to advance the fascial edges to their normal anterior, midline position, as shown in FIG. 8.

Although a step forward, the ABRA® device suffers from its placement within the abdomen, posing a threat to underlying intestinal structures, much like retention sutures. The company includes a large, protective silastic sheet to separate viscera from the elastic bands, but the silastic sheet, itself, has edges sitting within the abdomen that pose a risk to intra-abdominal contents. It is also not clear how the device would work in the absence of an open abdominal wound (elective hernia repairs), or in support of a difficult closure (fascia apposed but under high tension with high risk of failure).

FIG. 9 shows an example of abdominal wall anatomy and the various components.

SUMMARY OF THE INVENTION

In surgically supporting an incision or abdominal wound where there is a high risk of dehiscence, devices may be attached to the abdomen which span the incision or wound and apply tension in the direction of the midline, essentially functioning as an external, dynamic, and adjustable retention suture mechanism. Separately, in abdominal incisions or wounds for which high tension precludes primary closure, devices may be placed to approximate the edges of tissue towards one another in a manner which gradually apposes the edges for later repair under reduced tension.

The ideal corrective approach to anterior (ventral) abdominal wall defects would dynamically (non-rigid forces) maintain or bring abdominal wall components to their normal positions while:

a. Maintaining integrity of the abdominal wall structures (in contradistinction to component separation), b. Avoiding spanning materials deep to or in the plane of the abdominal wall so as to preclude device related injury to the underlying intestine or viscera, c. Avoiding mesh and its proclivity for complications, even years after surgery, d. In certain situations, allowing for support of the tissue closure even after surgical apposition to reduce the rate of recurrent fascial dehiscence (separation) while offering the potential to gradually transfer tension from the device to the incisional closure, and e. Being easily removed in the office or operating room when no longer necessary.

Generally, a first fixation member such as an elongate pin or structural member may be affixed at a first location through the abdominal wall near or at a first edge of an incision or wound. The fixation member may incorporate a backing or shoulder member which may provide support to maintain the fixation member in place within the tissue and prevent or inhibit the member from being pulled out of the tissue. A second fixation member, which may also be an elongate pin or structural member, may be affixed at a second location through the abdominal wall near or at a second edge of the incision or wound opposite the first location. The second fixation member may similarly incorporate a backing or shoulder member. The first and second fixation members may be secured to the tissue using various mechanisms such as medical balloons, screws, pins, hooks, compressive mechanism, etc. and as further described in detail below.

A connecting member (guide) may be adjustably securable to the first fixation member at a first connection and may also be adjustably securable to the second fixation member at a second connection. The connecting member may have a length sufficient to span the incision or wound while maintaining securement to the first and second fixation members in a transverse, non-parallel (to the wound), or angled orientation. Furthermore, the connecting member may be configured to provide a tensile or tensioning force to the first and second fixation members either simultaneously or singularly to a single fixation member while maintaining the transverse, non-parallel, or angled orientation. The tensile or tensioning force may be applied as a dynamic tension to the abdominal wall structures using various biasing mechanisms, as described in further detail herein (such as springs, elastic bands, ratcheting mechanism, etc.) where the application of the tensioning force is removed or remote or at a distance from where the first and second fixation members are secured to the tissue and is located outside of the abdominal wall plane. The tensioning force may be transmitted through the fixation members to the underlying tissue. Hence, the attachments may be moment-resisting to ensure that the apparatus has sufficient kinematic constraint. To ensure the device applies force to the abdominal wall while maintaining sufficient kinematic restraint, moment resisting features such as bars, rail mounted linear bearings, washers mounted anterior to the skin, multi-bar linkages, etc. may be utilized and as described in further detail herein.

That is, the first and second fixation members may be drawn or approximated towards one another via the application of the tensile or tensioning force along the connecting member while the orientation of the first and second fixation members relative to the connecting member remains unaltered. This enables the first and second fixation members to approximate the underlying tissue edges towards one another without the first and second fixation members collapsing onto the skin surface or wound.

While a tensile or tensioning force is described herein, other types of forces may be utilized such as compressive forces, shear forces, etc. through a number of different types of mechanisms for application to the fixation members for approximating the tissue.

Each of the guide securement supports may be slidingly secured on either side of an adjustable guide such as a rail or guide which may be positioned to extend directly over the wound or incision while supported by the guide securement supports. Each of the guide securement supports may include a guide securement attachment which extends from the support for attachment to any number of openings or other attachment mechanisms defined along a biasing member which may extend along the length of the adjustable guide between each of the supports and may also be attached to the adjustable guide between the supports. In this manner, the fixation member may be secured to the opposing edges of the wound or incision while the orientation of the fixation member may be maintained via their attachment to the guide securement support which are free to slide along the adjustable guide. When the guide securement attachment is attached to a respective opening or other attachment mechanism on both sides of the biasing member, the biasing member may apply a tensile or tensioning force to each of the respective guide securement supports such that they are drawn towards one another along the adjustable guide. This in turn transmits the tensile or tensioning force to the underlying tissue edges through the fixation members to approximate or support the edges of the wound or incision while maintaining an orientation of the fixation members relative to the underlying tissue.

As described, the biasing tensile or tensioning force is applied at a distance removed or remote from the surface of the wound or incision and the tensile or tensioning force is then transmitted directly to the underlying tissue via the fixation members. Accordingly, the height of the guide securement support may be adjusted such that the guide securement support and adjustable guide are positioned above the wound or incision.

Another variation of the apparatus may utilize an inflatable or expandable retention member to maintain a position of the fixation member relative to the tissue. An inflatable balloon or otherwise expandable member may be advanced through or along the fixation member for securing the apparatus to the tissue. In this variation, the balloon may have an elongate shaft with a valve member positioned at or near the opposite end of the device (from the balloon).

One variation of the tissue securement assembly may generally comprise a first fixation member having a first length, an anchor positionable near or at a proximal end (e.g., deep to the abdominal wall) of the first length and configurable between a delivery profile and an expanded anchoring profile, a guide securement support which is adjustably securable along a distal portion of the first length (e.g., above the surface of the abdominal wall), a guide having an elongate length and which is adjustably securable to the guide securement support, and a biasing member operably coupled along the guide securement support, wherein a tensioning force is applied by the biasing member to the guide securement support at a distance from tissue to be approximated.

Another variation of the tissue securement assembly may generally comprise a first fixation member having a first length, a tissue securement support which is adjustably securable along a portion of the first fixation member, a guide securement support which is adjustably securable along a distal portion of the first fixation member, an adjustable guide having an elongate length and which is adjustably securable to the guide securement support, and a biasing member operably coupled to the guide securement support, wherein a tensioning force is applied by the biasing member to the guide securement support and is transferred through the first length such that a dynamic (e.g., non-rigid, responsive to tissue retraction variations) tensioning force remains essentially constant or is adjustable to remain non-equilibrating. A variation of this assembly may comprise a system where the tissue securement support and guide securement support are combined into one support which accomplished both functions.

Another variation of the tissue securement assembly may generally comprise a first and second fixation member having a first and second length, a first and second tissue securement support which is adjustably securable along a portion of the first and second fixation member, a first and second guide securement support which is adjustably securable along another portion of the first and second fixation member, an adjustable guide having an elongate length and which is adjustably securable to the first and second guide securement support, and a biasing member which is securable along the adjustable guide to the first and second guide securement support such that a tensioning force applied to the first and second guide securement support by the biasing member is transferred through the first and second length of the first and second fixation member.

Another variation of the tissue securement assembly may generally comprise a first fixation member having a first length and defining a first lumen therethrough, an elongate shaft which is insertable through the first lumen and having an inflatable member near or at a proximal end of the elongate shaft which extends beyond the first lumen, a tissue securement support which is adjustably securable along a portion of the first fixation member, a guide securement support which is adjustably securable along a distal portion of the first fixation member, an adjustable guide having an elongate length and which is adjustably securable to the guide securement support, and a biasing member which is securable between the adjustable guide and the guide securement support such that a tensioning force applied to the guide securement support by the biasing member is transferred through the first length of the first fixation member.

Another variation of the tissue securement assembly may generally comprise a first and second fixation member having a first and second length and defining a first and second lumen therethrough, a first and second tissue securement support which is adjustably securable along a proximal portion of the first and second fixation member, a first and second guide securement support which is adjustably securable along a distal portion of the first and second fixation member, an adjustable guide having an elongate length and which is adjustably securable to the first and second guide securement support, and a biasing member which is securable between the adjustable guide and the first and second guide securement support such that a tensioning force applied to the first and second guide securement support by the biasing member is transferred through the first and second length of the first and second fixation member.

One variation of a method of approximating tissues of an open abdominal wall may generally comprise securing a first fixation member at a first tissue region in proximity to a first edge of a wound or incision, securing a second fixation member at a second tissue region in proximity to a second edge of the wound or incision opposite the first tissue region, coupling the first fixation member and the second fixation member to one another via an adjustable guide which spans a width of the wound or incision, wherein the adjustable guide is positioned at a height above the wound or incision such that the adjustable guide does not contact the abdominal contents, and applying a force to the first fixation member and the second fixation member along the adjustable guide which is removed from the wound or incision.

Another variation of a method of supporting an abdominal wall closure may generally comprise securing a first fixation member at a first tissue region in proximity to a first edge of a wound or incision, securing a second fixation member at a second tissue region in proximity to a second edge of the wound or incision opposite the first tissue region, coupling the first fixation member and the second fixation member to one another via an adjustable guide which spans a width of the wound or incision, and applying a force to the wound or incision via the adjustable guide which is also adjustable in height from the wound or incision such that the adjustable guide is positioned adjacent to or in proximity to the wound or incision.

Another variation of a method of approximating tissue may generally comprise securing a first fixation member at a first tissue region in proximity to a first edge of a wound or incision, securing a second fixation member at a second tissue region in proximity to a second edge of the wound or incision opposite the first tissue region, coupling the first fixation member and the second fixation member to one another via an adjustable guide which spans a width of the wound or incision, wherein the adjustable guide is positioned at a height above the wound or incision such that the adjustable guide does not contact the wound or incision, applying a tensioning force to the first fixation member and the second fixation member along the adjustable guide and above the wound or incision such that the tensioning force is transmitted dynamically through the first fixation member to the first tissue region and the second fixation member to the second tissue region, and approximating the first tissue region and the second tissue region towards one another. The same configuration can be used to support an incisional closure where the dynamic forces reduce tension across the incisional closure until such time as the tensile forces acting across the closure decline and/or the closure develops its own intrinsic strength.

BRIEF DESCRIPTION OF THE DRAWINGS

FIGS. 3A to 3C show abdominal wall component separation technique.

FIG. 4 shows a cross-sectional view of conventional treatment using mesh interposed within the abdominal wall to maintain closure.

FIGS. 12A to 12C show various perspective cross-sectional views of the tissue approximation apparatus.

FIGS. 21A and 21B show side and perspective views of the fixation member having the sharpened tip removed.

FIGS. 22A and 22B show side and perspective views of the fixation member having another variation of a removable sharpened tip.

DETAILED DESCRIPTION OF THE INVENTION

Figure 1:
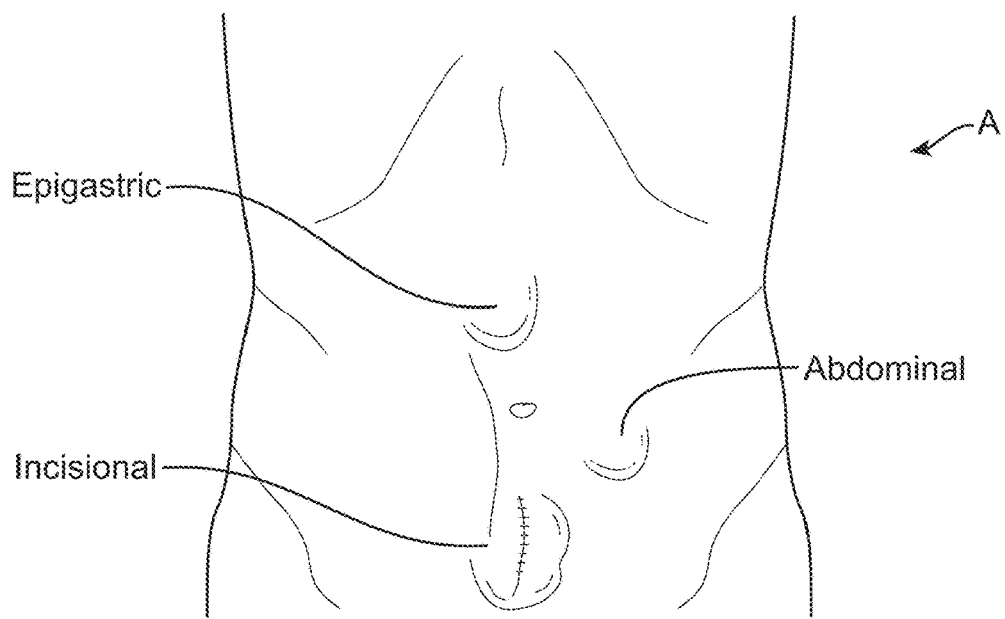
FIG. 1 an abdomen of a patient illustrating common sites for ventral hernias.
Figure 2:
FIG. 2 shows an example of mesh that has eroded into intestinal tissue.
Figure 5:
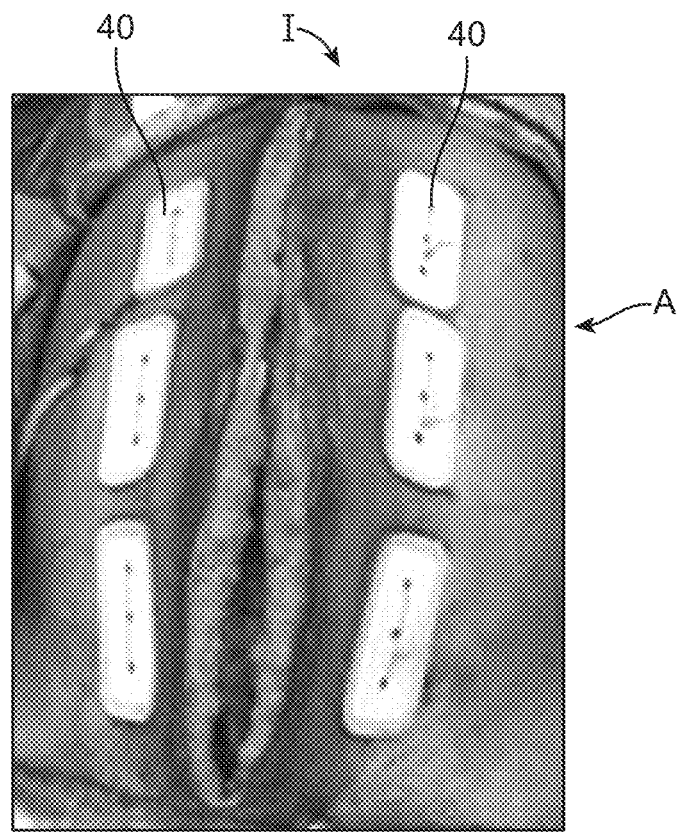
FIG. 5 shows an example of large sutures traversing the abdominal closure to hold tissue position during the early post-operative phases.
Figure 6:
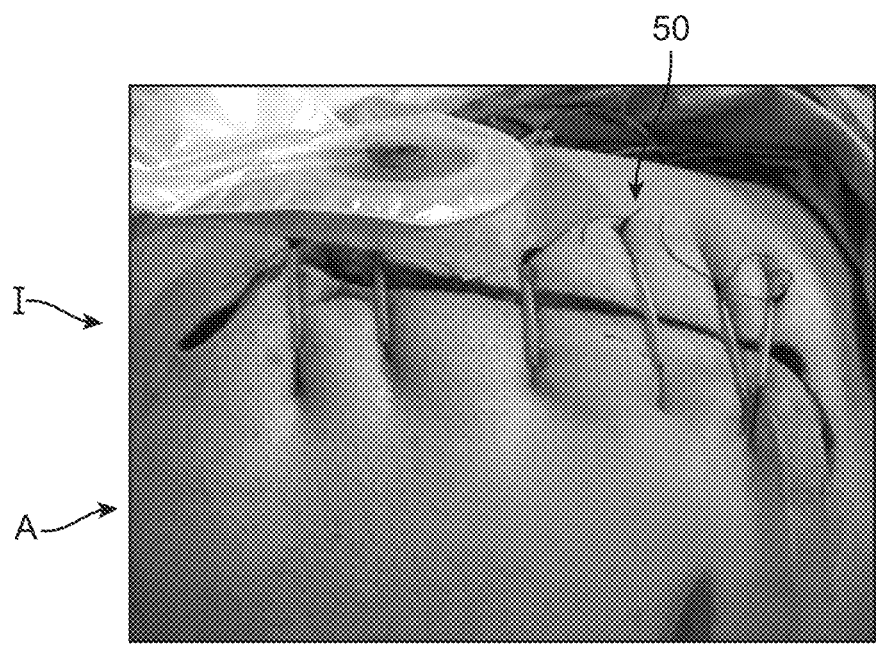
FIG. 6 shows retention sutures.
Figure 7:
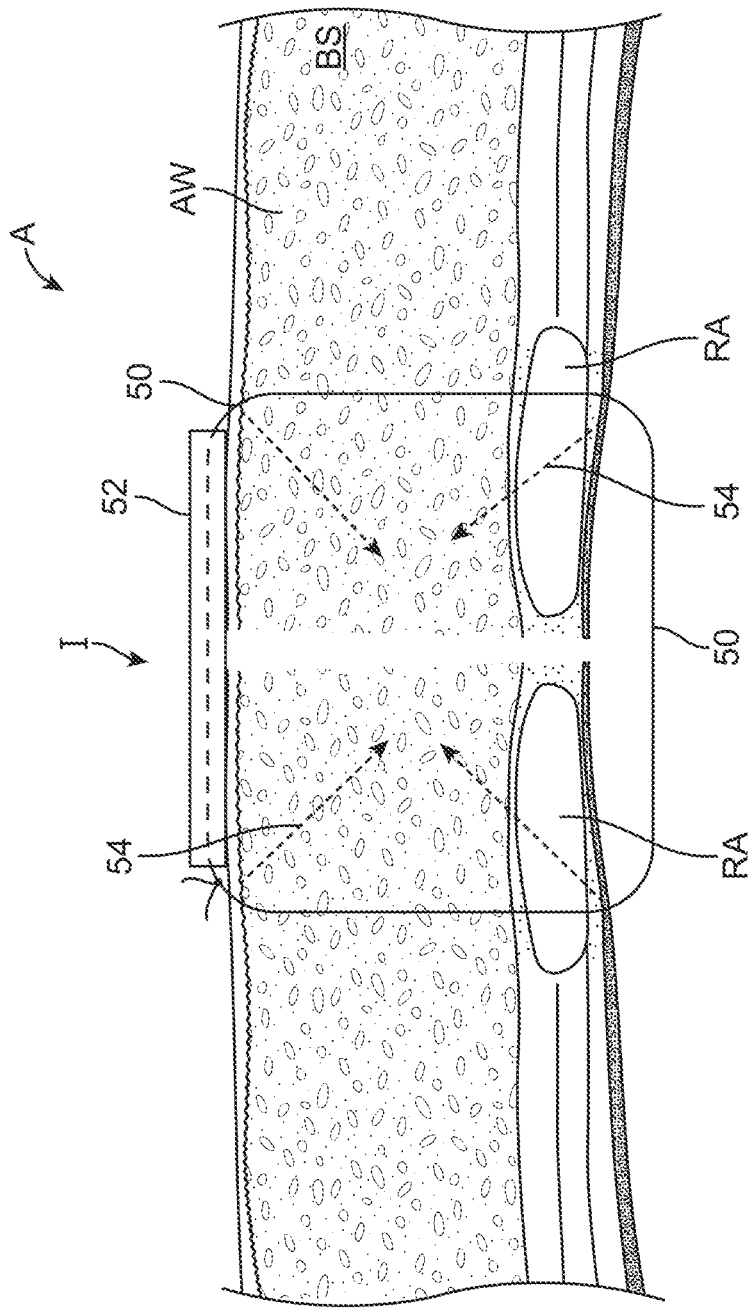
FIG. 7 shows an illustrative cross-sectional side view of a commonly used technique of placing retention sutures.
Figure 8:
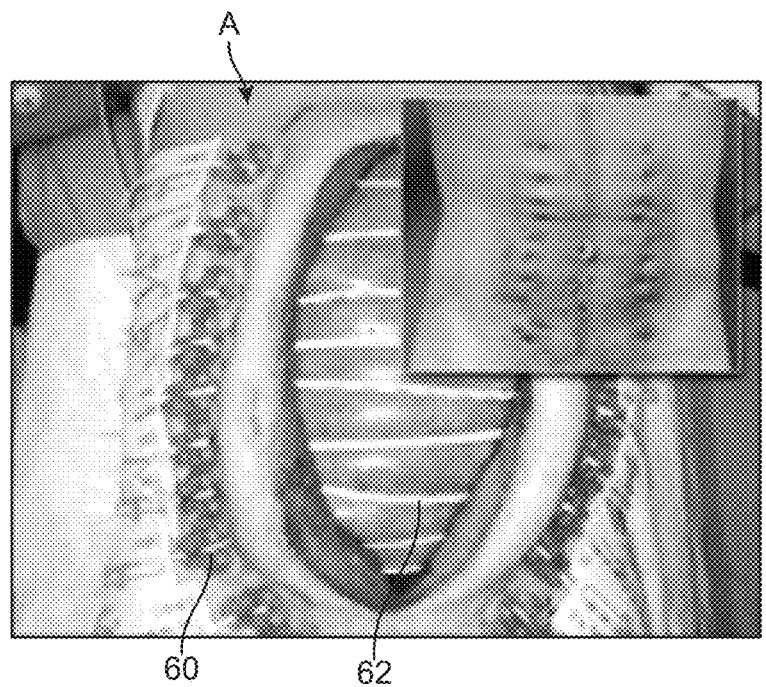
FIG. 8 shows an example of multiple elastic members crossing an open wound.
Figure 9:
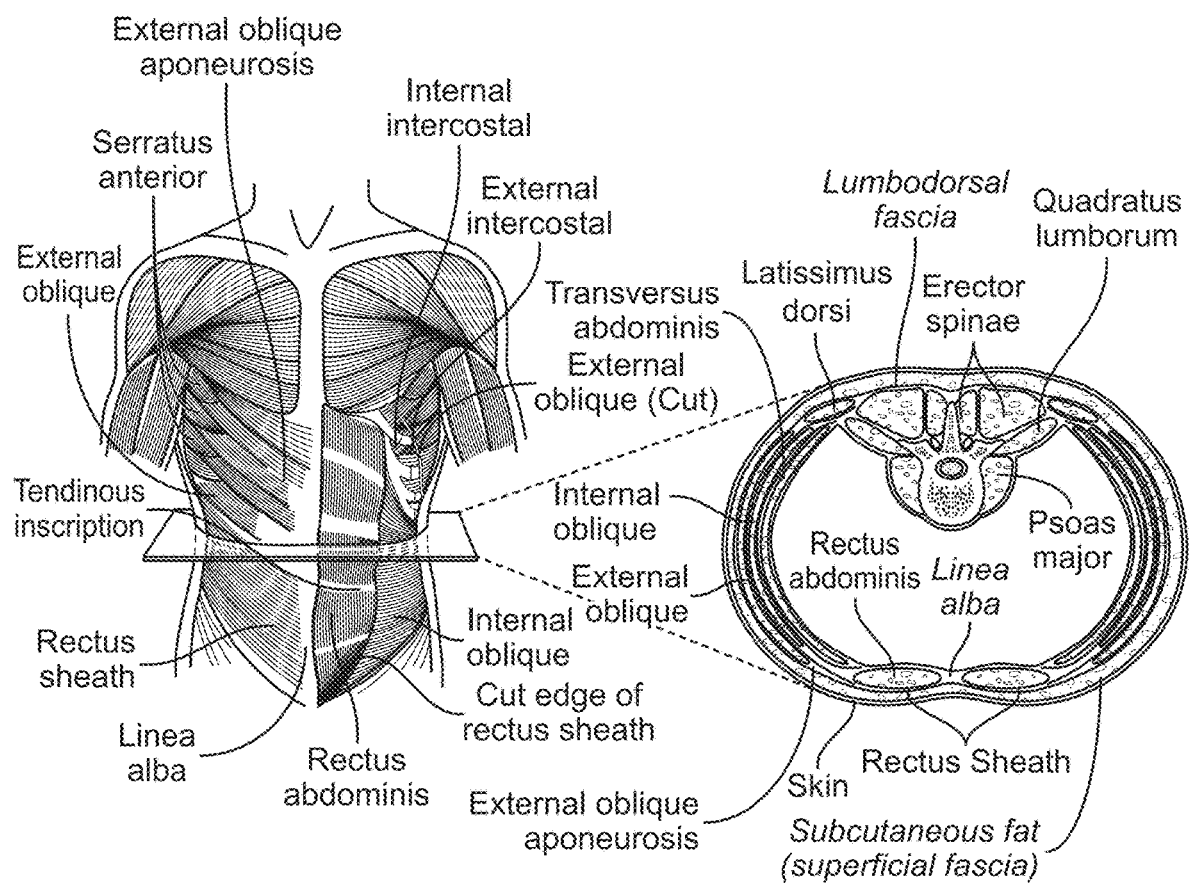
FIG. 9 shows an example of abdominal wall anatomy.
Figure 10A:
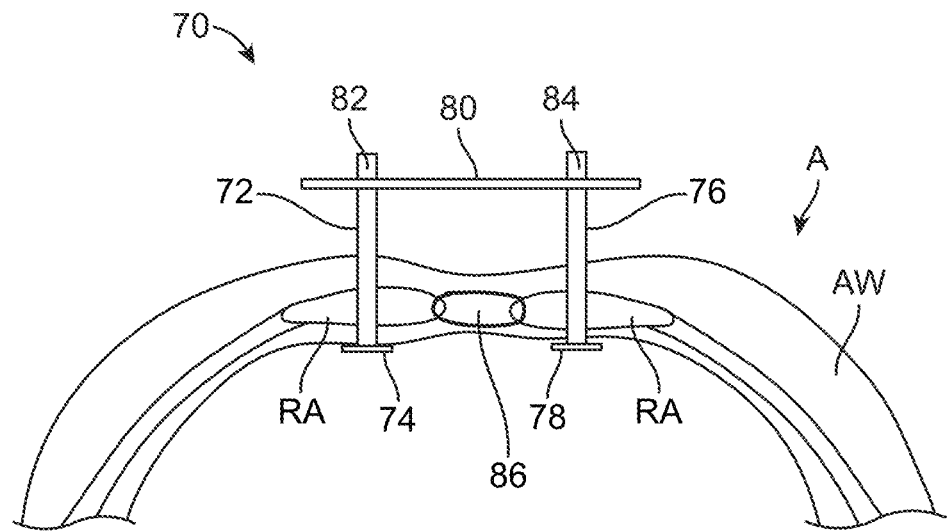
FIGS. 10A and 10B show general examples of the apparatus which allows for the repair of abdominal wall defects by applying dynamic forces well outside the abdominal cavity.

In the scenario where the surgeon is able to close the abdomen but perceives a high risk of dehiscence, the devices described herein may be attached to the abdomen, spanning the incision or wound, but the tension applied by the device to approximate the edges of tissue towards one another may be applied in a manner which reduces tension on the sutures (or other closure device), essentially functioning as an external, dynamic retention suture mechanism (FIG. 10A). The devices described herein may also be utilized to apply tension to close an incision or wound and allow for sutures or other closure device to be utilized after subject device has approximated the edges of the wound or incision.

Figure 10B:
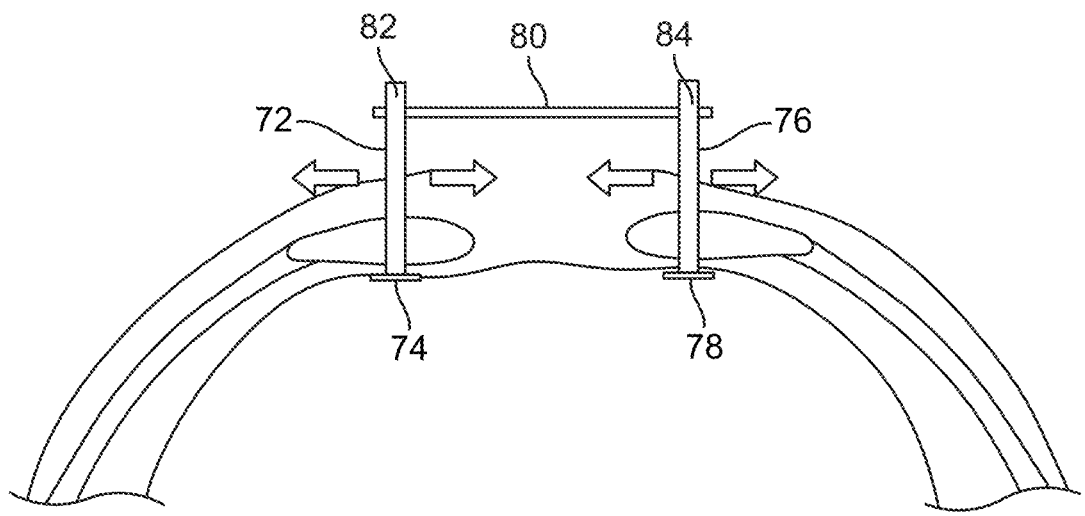

An example of gradual wound apposition is shown in the exemplary cross-sectional view of FIG. 10B which illustrates one variation of the apparatus described herein, allowing for the repair of abdominal wall defects by applying dynamic forces outside of the abdominal cavity and transferring these dynamic forces to the tissue edges. This allows for gradual elongation and apposition of the abdominal wall components to their normal anatomic positions without the presence of materials spanning the midline within or deep to the plane of the abdominal wall, thus greatly reducing the possibility of injury to intra-abdominal contents. It can be used in acute, open wounds (resulting, for example, from trauma, pancreatitis, etc.) or in high-risk surgical closures to support the midline structures until intra-abdominal pressures return to near normal or until healing or partial healing has occurred, thus preventing future ventral hernias. In certain circumstances, the apparatus could be used to facilitate elective ventral defect closures in which there is no open wound, but fascial edges are too far apart for simple closure.

Generally, a first fixation member 72 such as an elongate pin or structural member may be affixed at a first location through the abdominal wall AW such as a first rectus abdominis RA region near or at a first edge of an incision or wound. The fixation member 72 may incorporate a backing or shoulder member 74 which may provide support to maintain the fixation member 72 in place within the tissue and prevent or inhibit the member 72 from being pulled out of the tissue. A second fixation member 76, which may also be an elongate pin or structural member, may be affixed at a second location through the abdominal wall AW through a second rectus abdominis RA region near or at a second edge of the incision or wound opposite the first location. The second fixation member 76 may similarly incorporate a backing or shoulder member 78. The first and second fixation members 72, 76 may be secured to the tissue using various backing or shoulder mechanisms such as medical balloons, screws, pins, hooks, compressive mechanisms, etc. and as further described in detail below.

A connecting member 80 may be adjustably securable to the first fixation member 72 at a first connection 82 and may also be adjustably securable to the second fixation member 76 at a second connection 84. The connecting member 80 may have a length sufficient to span the incision or wound while maintaining securement to the first and second fixation members 72, 76 in a transverse, non-parallel (to the incision), or angled orientation. Furthermore, the connecting member 80 may be configured to provide a tensile or tensioning force to the first and second fixation members 72, 76 either simultaneously or singularly to a single fixation member while maintaining the transverse, non-parallel, or angled orientation, as shown in FIG. 10B. The tensile or tensioning force may be applied as an essentially constant tension to the abdominal wall structures using various biasing mechanisms, as described in further detail herein (such as springs, elastic bands, ratcheting mechanism, etc.) where the application of the tensioning force is removed or remote or at a distance from where the first and second fixation members 72, 76 are secured to the tissue and is therefore located outside of the abdominal wall plane. The tensioning force may be transmitted through the fixation members 72, 76 and transmitted to the underlying tissue. Hence, the attachments 82, 84 may be moment-resisting to ensure that the apparatus has sufficient kinematic constraint. To ensure the device applies force to the abdominal wall while maintaining sufficient kinematic restraint, moment resisting features such as bars, rail mounted linear bearings, washers mounted anterior to the skin, multi-bar linkages, etc. may be utilized and as described in further detail herein.

That is, the first and second fixation members 72, 76 may be drawn or approximated towards one another via the application of the tensile or tensioning force along the connecting member 80 while the orientation of the first and second fixation members 72, 76 relative to the connecting member 80 remains unaltered. This enables the first and second fixation members 72, 76 to approximate the underlying tissue edges towards one another without the first and second fixation members 72, 76 from collapsing onto the skin surface or wound.

Extension and apposition of the abdominal wall muscles is achieved gradually by applying the tensile or tensioning force using the first and second fixation members 72, 76 located within the full thickness of the abdominal wall. When surgical closure of the abdominal wall AW is accomplished, as shown in FIG. 10A, the surgery is greatly simplified since the abdominal wall tissues are now in their normal anatomic positions and relatively tension free. One or more sutures 86 or other fixation devices may be optionally applied to the approximated fascia and wound edges to facilitate wound closure.

Generally for scenarios where the fascial defect is closed as shown in FIG. 10A, the closure may be supported during the early post-operative period and the apparatus may be removed when it is no longer necessary.

On the other hand, generally for scenarios where the fascial defect and skin are open, as shown in FIG. 10B, a procedure may be used to approximate the leading edges of the fascial tissue and skin together by utilizing the apparatus as further described herein.

During the course of tissue approximation, as the tissue edges of the wound or incision are drawn towards one another, the tensioning force applied by conventional tissue approximation devices such as sutures or screws will naturally drop towards zero or the resting and/or muscular elastic recoil of the tissues, requiring frequent re-tensioning of the sutures or screws to maintain the desired tensile force upon the tissues.

However, the manner in which the tensioning force is applied to approximate the tissue edges of the wound or incision for the various embodiments described herein is such that the applied force remains essentially constant or above intrinsic tissue recoil forces (non-equilibrating) after application of the force over the course of treatment. This is due to the biasing mechanism, as described herein, which continues to apply the tensioning force to the fixation members and ultimately to the underlying secured tissues.

Figure 10C:
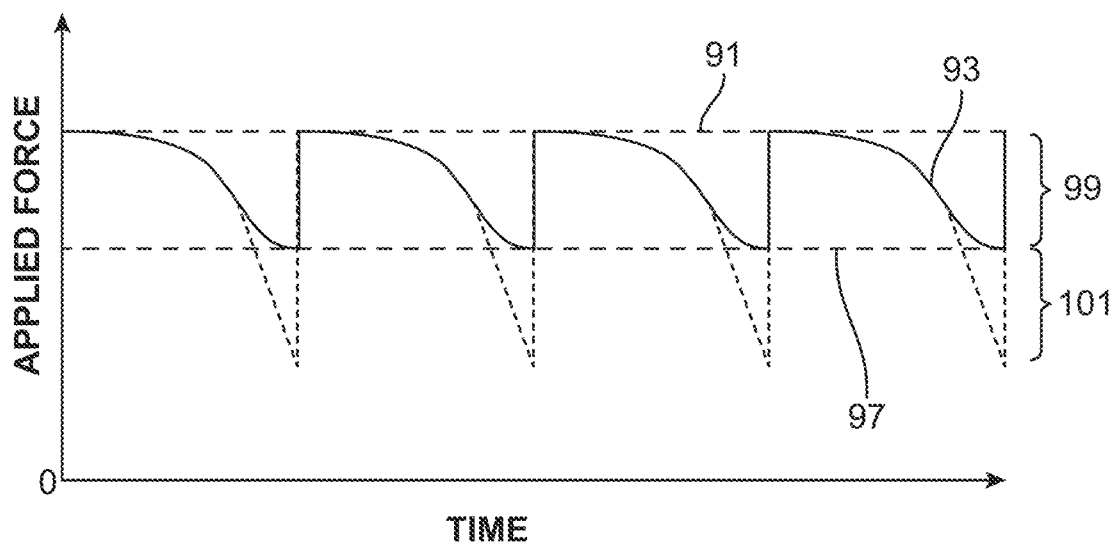
FIG. 10C shows an example of how the dynamic tensioning force may be applied to the tissue by the apparatus.

An example is shown in the graph of FIG. 10C which illustrates how the applied tensioning force using the devices herein may be applied such that the force remains either at a essentially constant level 91 or in a varying but non-equilibrating (above tissue recoil forcers) 93 manner where the apparatus may be adjusted as necessary to restore desired forces applied via the biasing mechanism. Although the applied force may decline over time or distance, because the biasing mechanism remains or is adjusted to maintain a force greater than tissue recoil forces, continuous gradual closure occurs rather than intermittent tissue advancement seen with other non-dynamic mechanisms. As the tissue wound edges approximate, there remains a threshold level 97 of force which may be applied to the tissue in order to draw the wound edges towards one another. An applied force below this threshold level 97 may be ineffective in approximating the tissue edges as it does not adequately exceed tissue recoil forces. With the application of the biasing mechanism, the imparted approximating force range which is effective 99 in drawing the wound edges towards one another may be maintained either continuously or over a relatively longer period of time above the threshold level 97 before falling below the threshold level 97 where the applied tensioning force range may become less effective 101.

This is in contrast to the graph of FIG. 10D which illustrates how the tensioning force using a conventional tissue approximation device such as sutures or screws will typically fall below the effective threshold level 97 (or that of the intrinsic recoil force of involved tissue) relatively quickly requiring their frequent re-tightening 95. This is due to the lack of a biasing mechanism which maintains the sutures or screws under an essentially constant and dynamic tensile or tensioning force. For example, a constant force spring could be utilized via a coil of material with a natural radius wound on a drum with a diameter larger than the natural diameter. Once the extension of the tail of the material from the coil exceeds, e.g., approximately 1.25 times the drum diameter, the force that causes the spring to retract is constant. At less than, e.g., 1.25 times the drum diameter, the force may fall towards zero in a non-linear manner. By careful selection of natural radius and drum diameter the force exerted by the spring over linear distances needed to close the wound, the force in working range can be maintained at a steady level which is at or near constant. This is illustrated by the region of the curve shown above the threshold level 97 as the imparted approximating force range 99' which is effective in drawing the wound edges towards one another as compared to the ineffective tensioning force range 101' shown below the threshold level 97 which amounts to a greater period of time of ineffective tissue approximation.

Figure 10D:
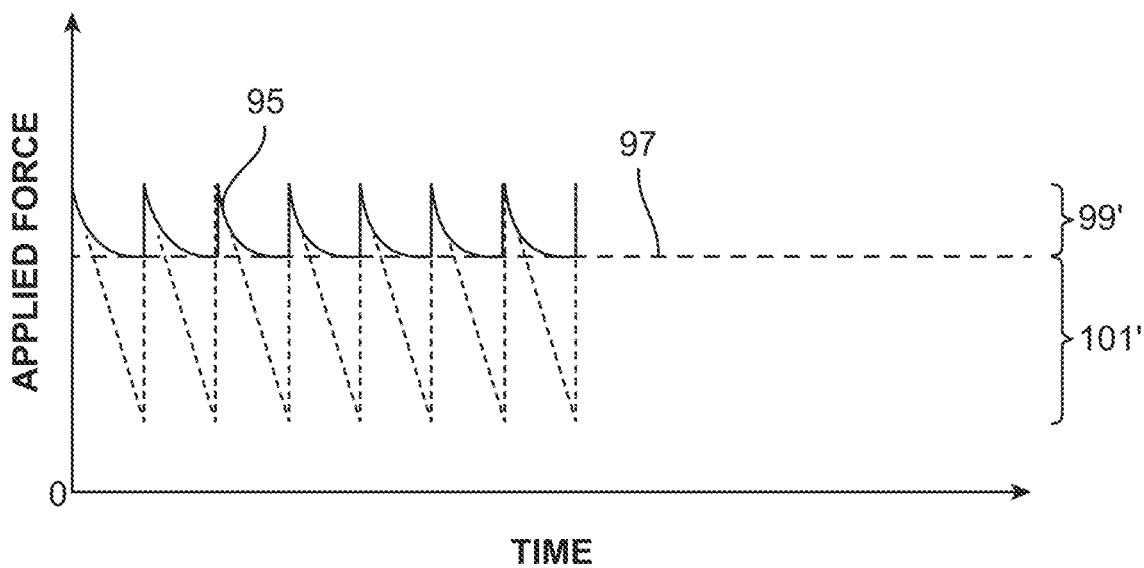
FIG. 10D shows an example for contrasting how a conventional tissue approximation device applies force to the tissue and requires frequent tightening to maintain the tissue approximation force on the tissue.

The maximum amount of force applied by the biasing mechanism shown in FIG. 10C may thus be at a level which is relatively lower (e.g., 50% to 90% of conventional methods) than the maximum amount of force applied by conventional tissue approximation devices shown in FIG. 10D which results in greater comfort to the patient and lower risk of tissue injury. However, even with the relatively lower maximum force applied, the biasing mechanism may apply an effective amount of approximating force 99 for a relatively longer period of time (e.g., 50% to 100% longer) when compared to the conventional tissue approximation devices.

In addition, a system utilizing screws or sutures will fail to yield if tension in the tissues increases (for example if the patient coughs or moves) due to their unyielding mechanisms, for example, if the opposite edges of the wound were drawn apart or at an angle relative to one another by the movement. This unyielding nature imparts the force experienced directly to the anchored muscles and tissue and because the anchored tissues are secured and unmoving relative to one another, the tension or shear forces experienced by the patient may be felt dramatically resulting in pain and can also result in tissue tearing. On the other hand, the dynamic biasing forces of the described invention will dynamically yield during increases in tissue tension due to the ability of the anchors to move relative to one another, as shown by the arrows in FIG. 10B, towards or away from one another. This ability to move and adjust while still maintaining a biasing force on the tissue may result in an alleviation of any excessive imparted external forces and reduce pain and tissue damage.

Figure 11:
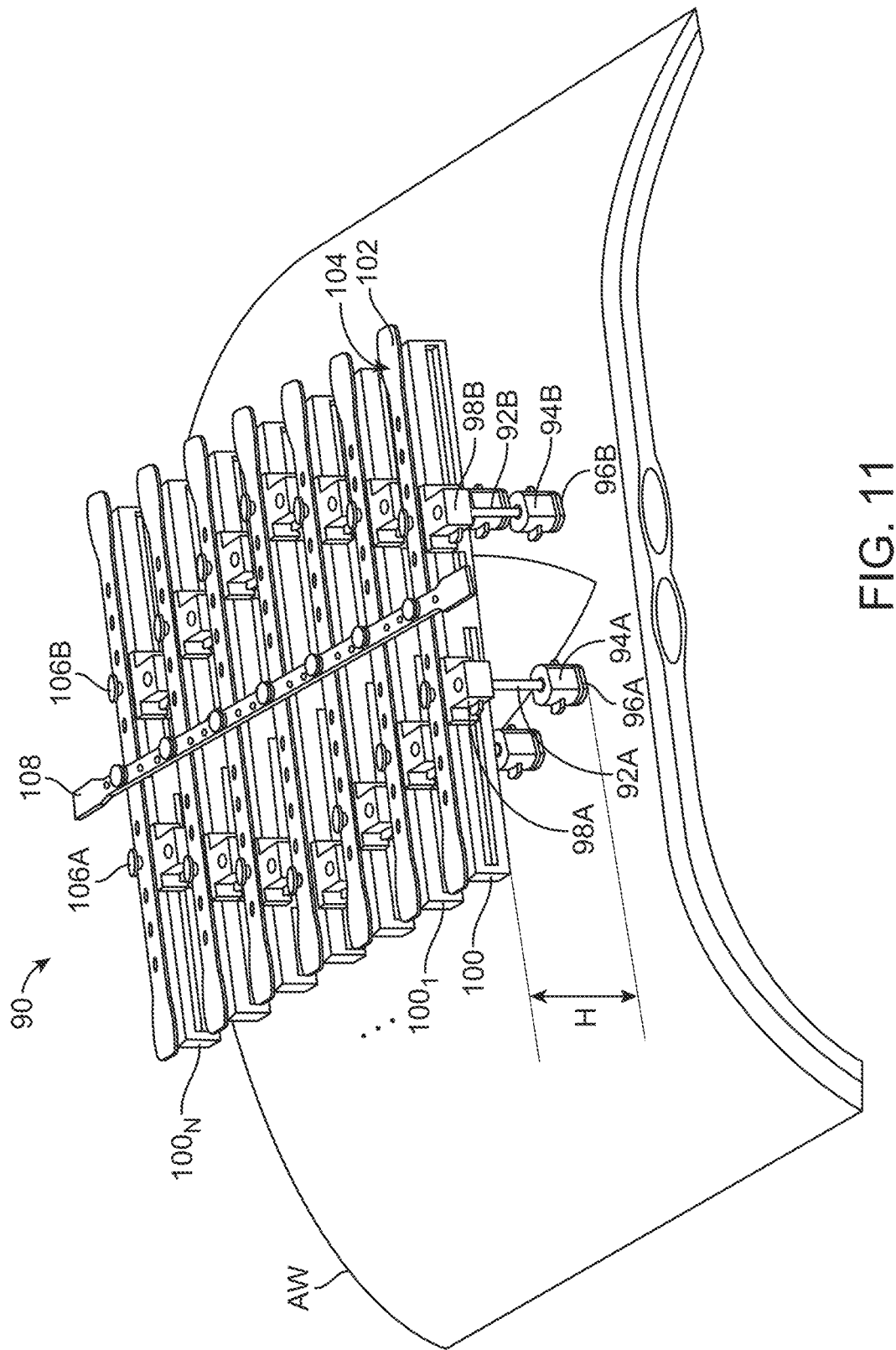
FIG. 11 shows an embodiment of a tissue approximation system which may utilize a first and second fixation member which may be secured at first and second respective locations on opposite sides of a wound or incision in proximity to the respective edges.

Turning to one variation of the apparatus, FIG. 11 shows an embodiment of a tissue approximation system 90 which may utilize a first and second fixation member 92A, 92B which may be secured at first and second respective locations on opposite sides of a wound or incision in proximity to the respective edges. The first and second fixation member 92A, 92B may be each inserted into the abdominal wall and secured in place in part by a tissue securement support 94A, 94B through which the fixation member 92A, 92B may be slidingly insertable through and selectively secured to prevent further movement of the fixation member relative to the tissue securement support. Each of the tissue securement supports 94A, 94B may incorporate an interface member 96A, 96B made from a soft and atraumatic material (e.g., foam, pads, silicone, fluid-filled balloon, etc.) to cushion the interface member 96A, 96B against the surface of the skin and to possibly elute antiseptics to reduce risk of pin track infection. In addition, to accommodate patient movement during dynamic events (e.g., bending over, coughing, etc.), atraumatic features such as interface member 96A, 96B may prevent direct impingement or rubbing of the device against the skin.

The first and second fixation members 92A, 92B when secured relative to the tissue may project away from the skin surface such that a guide securement support 98A, 98B may also be slidingly positioned upon a portion of the fixation members 92A, 92B, as shown.

Each of the guide securement support 98A, 98B may be slidingly secured on either side of an adjustable guide 100 such as a rail or guide which may be positioned to extend directly over the wound or incision while supported by the guide securement support 98A, 98B. Each of the guide securement support 98A, 98B may include a guide securement attachment 106A, 106B which extends from the support 98A, 98B for attachment to any number of openings 104 defined along a biasing member 102 which may extend along the length of the adjustable guide 100 between each of the supports 98A, 98B and may also be attached to the adjustable guide 100 between the supports 98A, 98B, e.g., biasing member 102 may be attached to guide 100 near its center. In this manner, the fixation member 92A, 92B may be secured to the opposing edges of the wound or incision while the orientation of the fixation member 92A, 92B may be maintained via their attachment to the guide securement support 98A, 98B which are free to slide along the adjustable guide 100. When the guide securement attachment 106A, 106B is attached to a respective opening 104 on both sides of the biasing member 102, the biasing member 102 may apply a dynamic and essentially constant tensile or tensioning force to each of the respective guide securement support 98A, 98B such that they are drawn towards one another along the adjustable guide 100, e.g., a tensile or tensioning force of 100 to 400 grams may be applied. This in turn transmits the tensile or tensioning force to the underlying tissue edges through the fixation members 92A, 92B to approximate the edges of the wound or incision while maintaining an orientation of the fixation members 92A, 92B relative to the underlying tissue.

Furthermore, the amount of tensile or tensioning force applied may be varied over the length of treatment. For instance, an initial tensile or tensioning force of, e.g., 150 to 300 grams, may be applied at the initial treatment when the fixation members 92A, 92B are first inserted within the tissue. After a period of time as the edges of the wound begin to approximate towards one another, the amount of tensile or tensioning force applied may be maintained at the same level or reduced by, e.g., 50%, by adjusting an attachment position of the guide securement support 98A, 98B along the biasing member 102.

To impart the biasing tensile or tensioning force, the biasing member 102 may be configured as, e.g., a lead screw, ratcheting system, springs (such as wind-up springs, torsional springs, constant force springs, etc.), or other structural member, etc. Alternatively, the biasing member 102 may include, e.g., elastic bands, elastomers, etc., so long as it provides an essentially constant and dynamic biasing force transmitted to the underlying tissue regardless of movement of the fixation members 92A, 92B towards or away from one another. Another embodiment may see the guide member consisting of a geared rack and the connector including a geared pinion driven directly or indirectly by a spring or other elastic member. The torque on the pinion gear applies the dynamic force to cause the connector to move along the guide member.

With wounds or incisions extending along the abdominal surface, any number of tissue approximation apparatus, e.g., 100I to 100N, may be implemented depending on the length of the wound or incision. The variation shown in FIG. 11 illustrates seven individual apparatus applied over the length of the wound or incision; however, the actual number used may vary. The individual tissue approximation apparatus may be spaced apart from an adjacent apparatus along the length of the wound or incision, e.g., 2 to 6 cm apart. As the distance between the edges of the wound or incision may vary depending on the location, e.g., the tissue edges near the ends of the wound or incision may be relatively closer to one another than the edges near the center region of the wound or incision, the positioning of the guide securement support 98A, 98B along the adjustable guide 100 may be varied to accommodate the spacing between the tissue edges of the underlying wound or incision. This may be done so long as the guide securement support 98A, 98B is maintained under a essentially constant tensile or tensioning force by a respective biasing member which may be adjusted to couple to the guide securement support 98A, 98B to an appropriate opening 104 along the biasing member 102. Hence, the guide securement support may be positioned relative to an adjacent support to track the edges of the underlying wound or incision while maintaining an essentially constant tensile or tensioning force over the edge of the entire wound or incision. Alternatively, different amounts of tensile or tensioning force may be applied at different locations along the edge of the wound or incision, if necessary or desired.

With multiple apparatus applied to a wound or incision, each of the adjustable guides may be coupled to one another via an adjustment guide 108 which may extend over each of the adjustable guides along the length of the wound or incision, as shown.

As described, the biasing tensile or tensioning force is applied at a distance removed or remote or at a distance from the surface of the wound or incision and the essentially constant or non-equilibrating (relatively to intrinsic tissue recoil forces) tensile or tensioning force, as described herein, is then transmitted directly to the underlying tissue via the fixation members 92A, 92B. Accordingly, the height of the guide securement support 98A, 98B above the surface of the wound or incision may be adjusted to any height H so long as the adjustable guide 100 is positioned above the wound or incision and not in contact with the underlying abdominal contents. The height H may be adjusted and secured at various heights depending on the amount of clearance from the underlying tissue, for example, for accessing the tissue region for cleaning or accessing the devices as well as managing the underlying wound. As such, the height H may be adjusted to have some minimum height clearance above the underlying tissue surface, e.g., 1 to 10 cm. Alternatively, the height H may be adjusted for each of the devices to be uniform with respect to one another. In any case, the height H may remain fully adjustable relative to the underlying tissue surface.

The adjustable guide 100, in some cases, may be removed entirely by releasing the guide securement support 98A, 98B from the fixation members 92A, 92B while the guide securement support 98A, 98B remain attached to the adjustable guide 100. The fixation members 92A, 92B may remain secured to the tissue, this allows for the underlying tissue to be easily accessed. Once a procedure has been completed upon the underlying tissue, the guide securement support 98A, 98B and adjustable guide 100 may be reattached to the fixation members 92A, 92B and tension re-applied for approximating the tissue. Other variations may allow for removal and subsequent reattachment of only the guide 100 from the underlying device components.

FIGS. 12A to 12C show various perspective cross-sectional views of the tissue approximation apparatus illustrating how the fixation members 92A, 92B may incorporate a backing or shoulder 109A, 109B having a diameter which is larger than a diameter of the fixation members 92A, 92B. The backing or shoulder 109A, 109B may present an atraumatic configuration which prevents damage to adjacent or adjoining tissues such as any abdominal tissue which may be in proximity to the fixation members 92A, 92B during deployment or fixation.

With the apparatus implanted into the patient, the system may optionally include various patient interaction features such as safety features, atraumatic pin tips, snag protection features, etc. For instance, to prevent a patient from intentionally or inadvertently damaging or tampering with the device, safety features such as covers, fastener heads, etc. may be utilized.

Another feature may include various mechanisms to prevent or inhibit the patient from intentionally or inadvertently pressing against the device after implantation which could cause the apparatus from being pressed internally within the abdominal cavity and potentially causing damage to portions of the bowel or other organs in proximity to the fixation members. To address this potential risk, various securement mechanisms may be used individually or in combination.

In one variation, a device such as a tonometer could be used to measure pressure applied to the outer layer of exposed tissue and aid in preventing excessive compression and tissue damage. Pressures on tissue of less than, e.g., 32 mm Hg, typically do not cause necrosis and as such, tonometer levels at or below that reading would allow for ideal deployment. The tonometer may thus help to set a sub-injurious level of compression of the tissue sandwiched between the tissue securement supports 94A, 94B and backstop or shoulder 109A, 109B.

As previously described, the interface member 96A, 96B may be positioned between the tissue securement supports 94A, 94B and the underlying tissue to present an atraumatic interface as well as to distribute any forces over the interface member 96A, 96B against the tissue. The interface member 96A, 96B may be pre-loaded to a compressive force that is below a threshold level which would otherwise cause local ischemia or injury to the tissue. This interface member 96A, 96B may also have antimicrobial compounds on the surface or within to prevent infection at the pin site (e.g., Biopatch®, Johnson & Johnson Corp., NJ). Additionally and/or optionally, the interface member 96A, 96B may be configured as transparent or translucent padding having an irradiating light incorporated to illuminate the skin surrounding the skin fenestration area with, e.g., UV light, for reduction or elimination of harmful bacteria in this region. A battery could power a UV LED source for clinical effect for several days or weeks.

Additionally and/or optionally, a protective covering or shell may be applied around the entire external apparatus to prevent any inadvertent forces from acting upon the individual elements or regions of the device. If the covering or shell completely encloses the apparatus, then the outer perimeter of the turtle shell may contact the torso first if there is an external load put on the shell and prevent contact against the apparatus. The edges of the covering or shell may momentarily contact and press the tissue well outboard of the wound zone and the external apparatus resulting in no fixation member displacement and only minor patient discomfort of the covering or shell contact with healthy tissue.

Additionally and/or optionally, the lengths of the fixation members 92A, 92B and/or the guide member 100 may be adjusted to accommodate different patient anatomy. The lengths of the fixation members 92A, 92B and/or guide member 100, for instance, may be shortened using various methods such as snap-off lengths, if needed or desired, as also described below in further detail. Alternatively, a number of individual lengths of the fixation members 92A, 92B and/or the guide member 100 may be coupled to one another to form an elongated fixation members 92A, 92B and/or the guide member 100, if needed or desired. As further described herein, each of the guide securement support 98A, 98B may be adjusted in height above the surface of the tissue, and/or the fixation members 92A, 92B themselves may be adjusted in height as well or different lengths of the fixation members 92A, 92B and/or the guide member 100 may be used.

Figure 13:
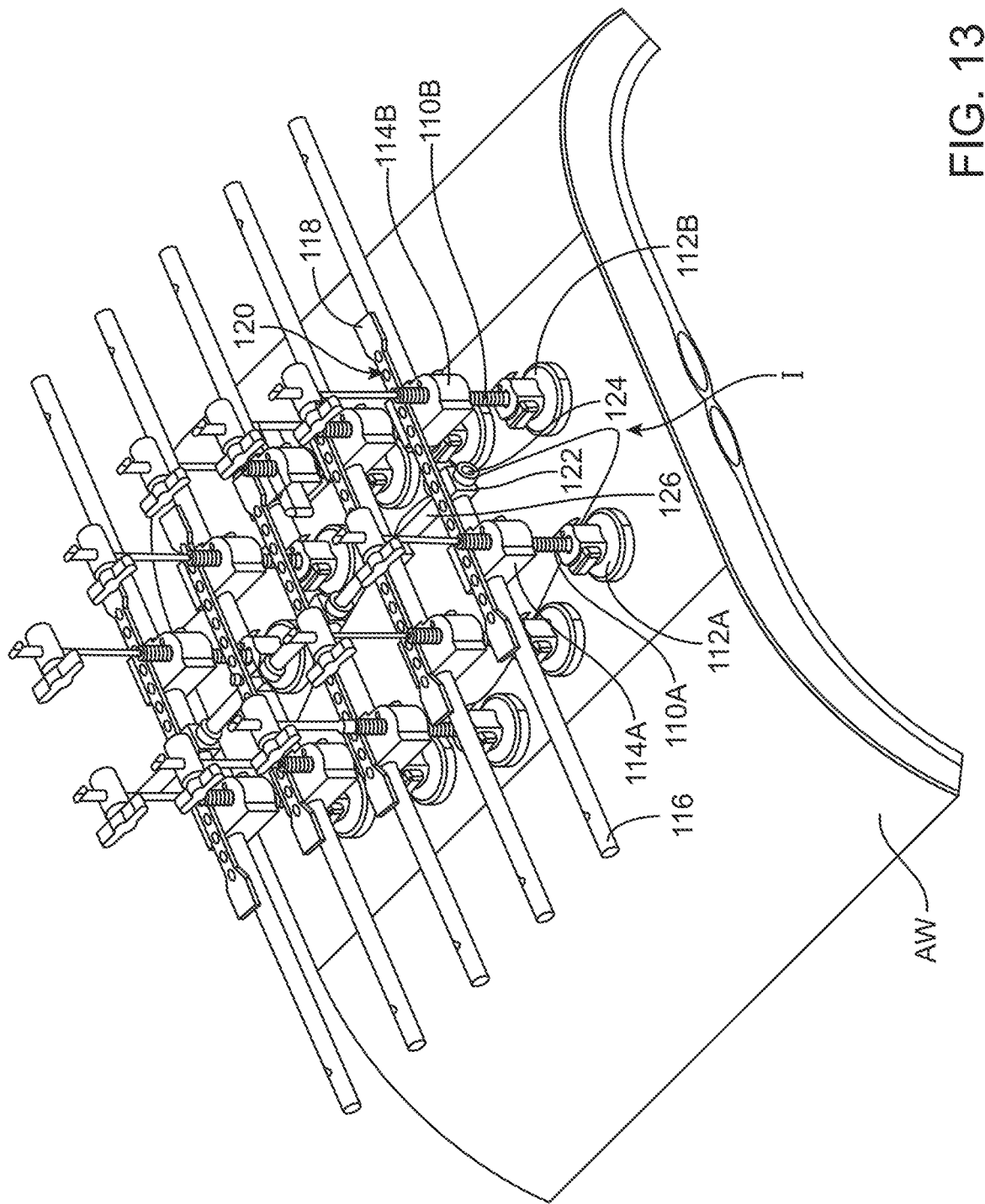
FIG. 13 shows the anterior view of another variation of the tissue approximation system utilizing an inflatable or expandable retention member to maintain a position of the fixation member (not shown in this angle).

Another variation of the apparatus is shown in the perspective view of FIG. 13 which illustrates an apparatus utilizing an inflatable or collapsible retention member 132A, 132B (in other illustrations) to maintain a position of the fixation member 110A, 110B relative to the tissue, as described in further detail below. The fixation member 110A, 110B (which may define a lumen through the length of each fixation member 110A, 110B) may be attached to tissue securement supports 112A, 112B which may maintain the fixation member 110A, 110B in place against the tissue surface and to guide securement support 114A, 114B which are slidingly coupled to adjustable guide 116 which may be configured as an elongate tubular member in this variation. The guide securement support 114A, 114B may be secured to biasing member 118 through a number of openings 120 which are selectable to adjust a length and essentially constant or non-equilibrating tensioning force of the guide securement support 114A, 114B relative to one another. The biasing member 118 may span directly between securement support 114A, 114B or may have an intermediate attachment near the center of guide 116 via an attachment 130 (shown in FIG. 14).

Furthermore, in this variation, the adjustable guide 116 may incorporate an alignment member 122 positioned between the guide securement support 114A, 114B. The alignment member 122 may further define one or more receiving openings 124 for receiving connecting members 126 for attachment to an adjacent adjustable guide 116. Similarly, as described above, the variation shown in FIG. 13 may be used with one or more tissue approximation devices each having individually adjustable guide securement supports. If two or more devices are used to approximate the underlying wound or incision, they may be connected to adjacent devices via connecting members 126 coupling to one another.

Figure 14:
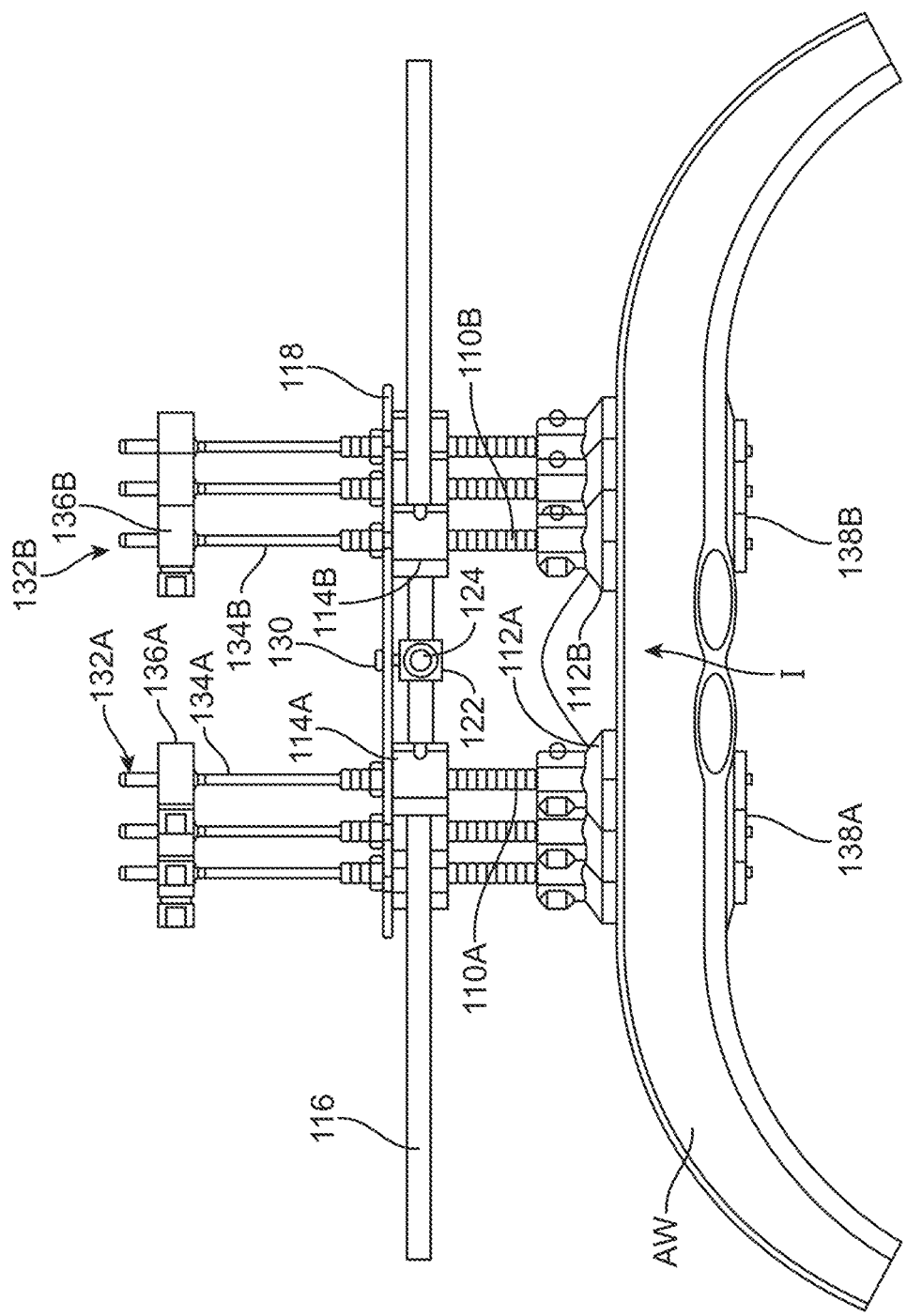
FIGS. 14 and 15 show partial side and perspective views of the device variation.
Figure 15:
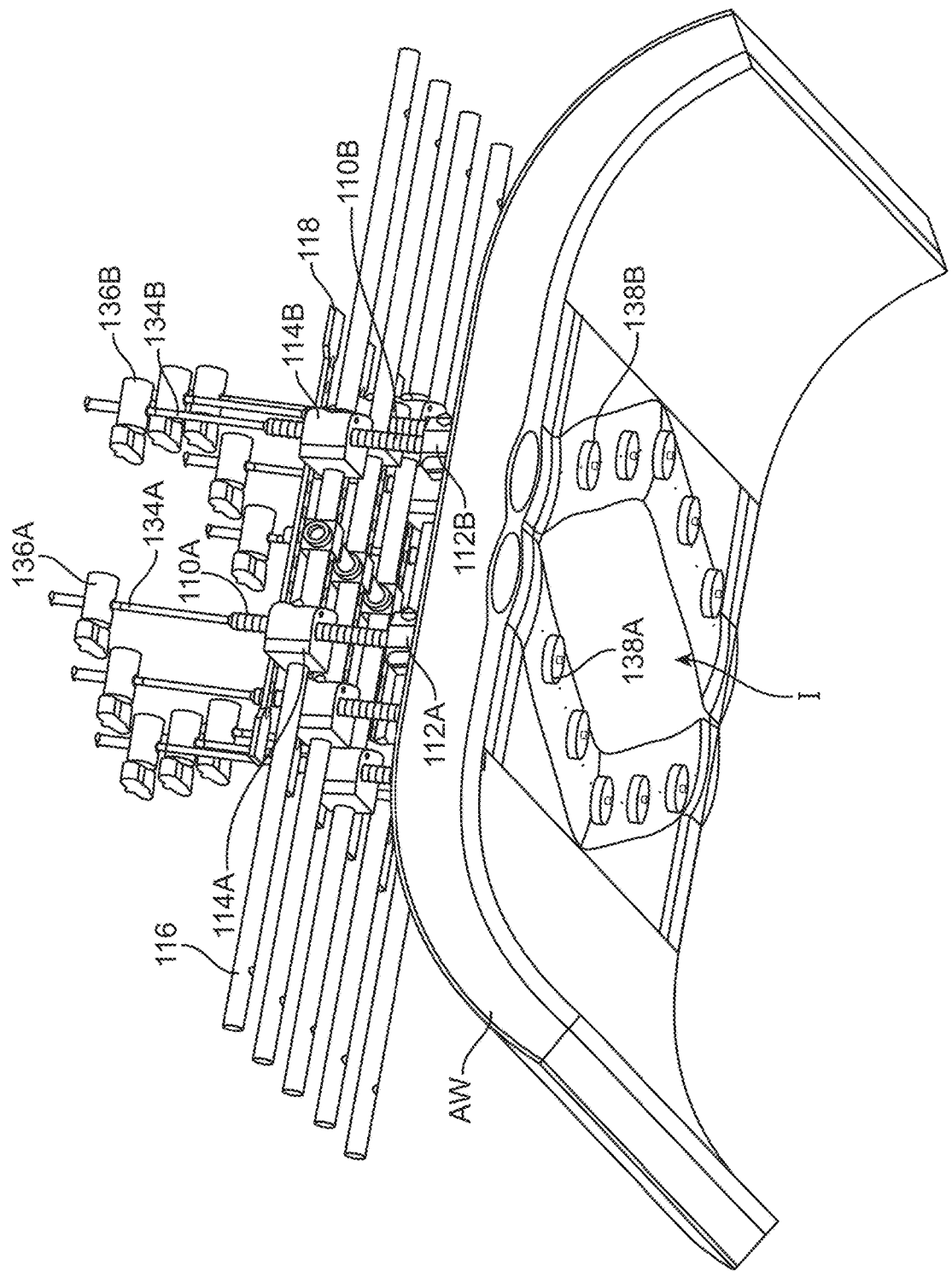
Figures 19, 20:
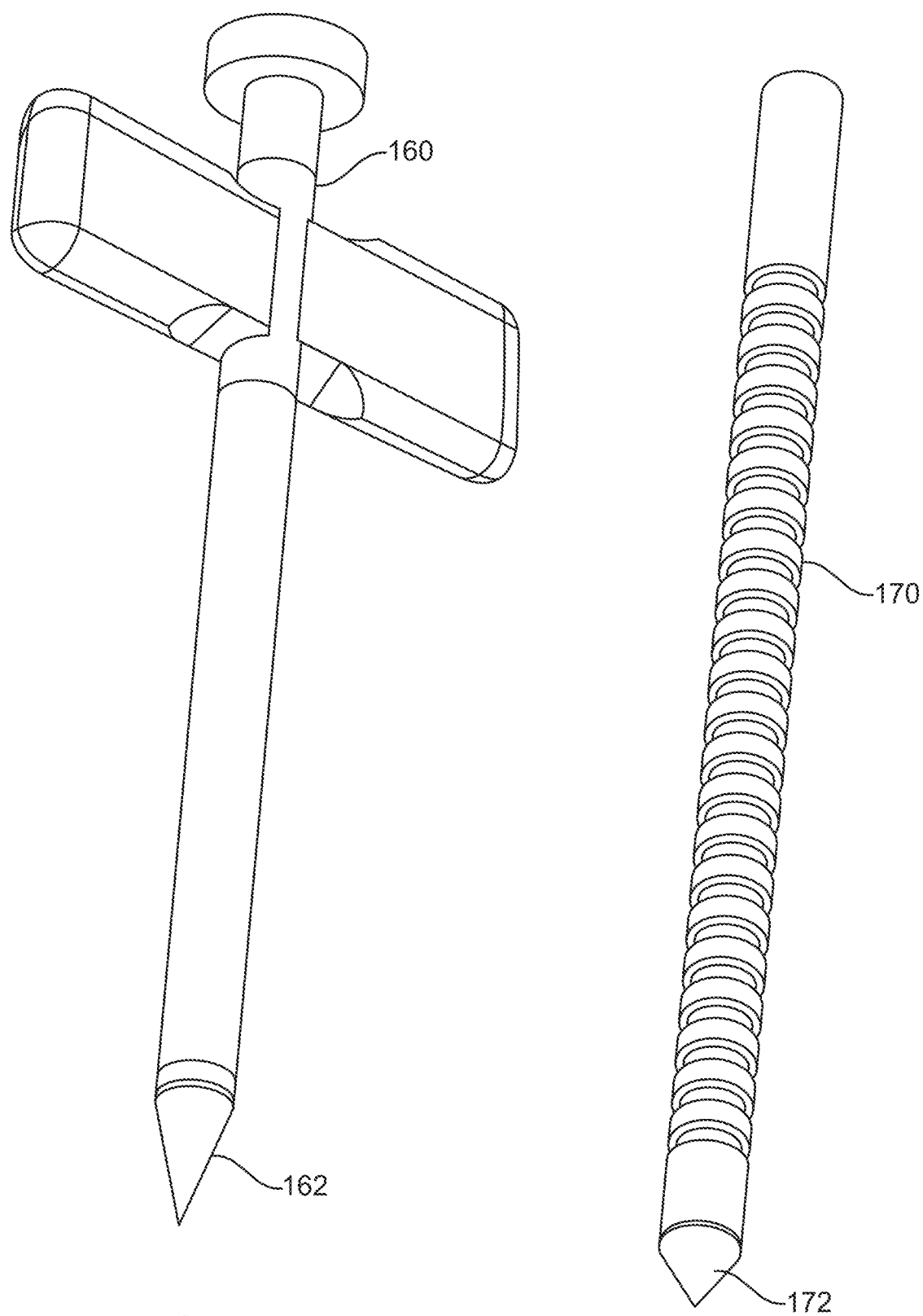
FIG. 19 shows a perspective view of a trocar having a sharpened introducer tip.
FIG. 20 shows a perspective view of a fixation member having a sharpened tip.

FIGS. 14 and 15 show partial side and perspective views of the device variation illustrating how an additional inflation member 132A, 132B having an inflatable balloon 138A, 138B or otherwise expandable member located on its end may be advanced through the fixation member 110A, 110B for securing the apparatus to the tissue. In this variation, the inflation member 132A, 132B may each have an elongate shaft 134A, 134B with a valve member 136A, 136B positioned along at the other end of the device. The fixation member 110A, 110B may be initially introduced through the tissue using, e.g., a trocar 160 having a sharpened introducer tip 162 (as shown in the perspective view of FIG. 19) which may be removed after insertion. Alternatively, the fixation member 110A, 110B may be introduced directly into the tissue via a variation of the fixation member 170 having a sharpened tip 172 (as shown in the perspective view of FIG. 20) which may be removed after insertion such as an obturator being removed from a trocar, or it may be covered with a threaded cap that serves as the internal fixation member. FIGS. 21A and 21B show side and perspective views of one example of a fixation member 170 having the removable tip 172 which may be inserted securely within a lumen defined through the fixation member 170. FIGS. 22A and 22B show side and perspective views of another example of a fixation member 170 having a removable tip 180 which may be secured over a tip of the fixation member 170.

In either case, the fixation member 110A, 110B may define a hollow lumen through which the inflation member 132A, 132B may be advanced after placement of the fixation member 110A, 110B. With the end of the inflation member 132A, 132B inserted into the abdominal cavity, the inflatable balloon 138A, 138B may be expanded via the introduction of a liquid or gas through the elongate shaft 134A, 134B. After inflation, the valve member 136A, 136B may be closed to maintain the expanded configuration of the balloon 138A, 138B against the interior surface of the tissue. The inflation member 132A, 132B may be secured to the fixation member 110A, 110B to maintain traction of the device relative to the tissue.

Figure 16A:
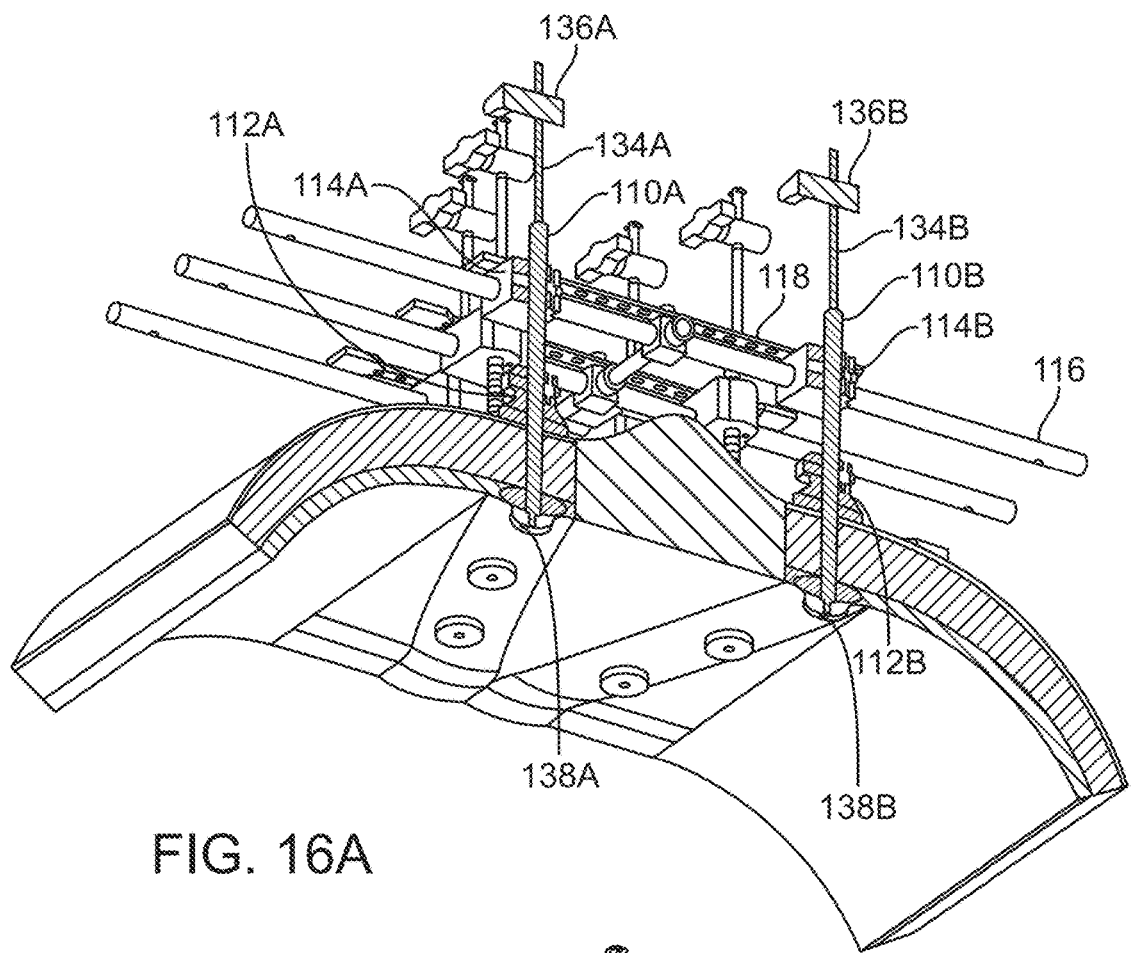
FIGS. 16A and 16B are partial cross-sectional perspective views illustrating how an internal channel may extend through the fixation member to an inflatable securement member in contact with the interior tissue surface.
Figure 16B:
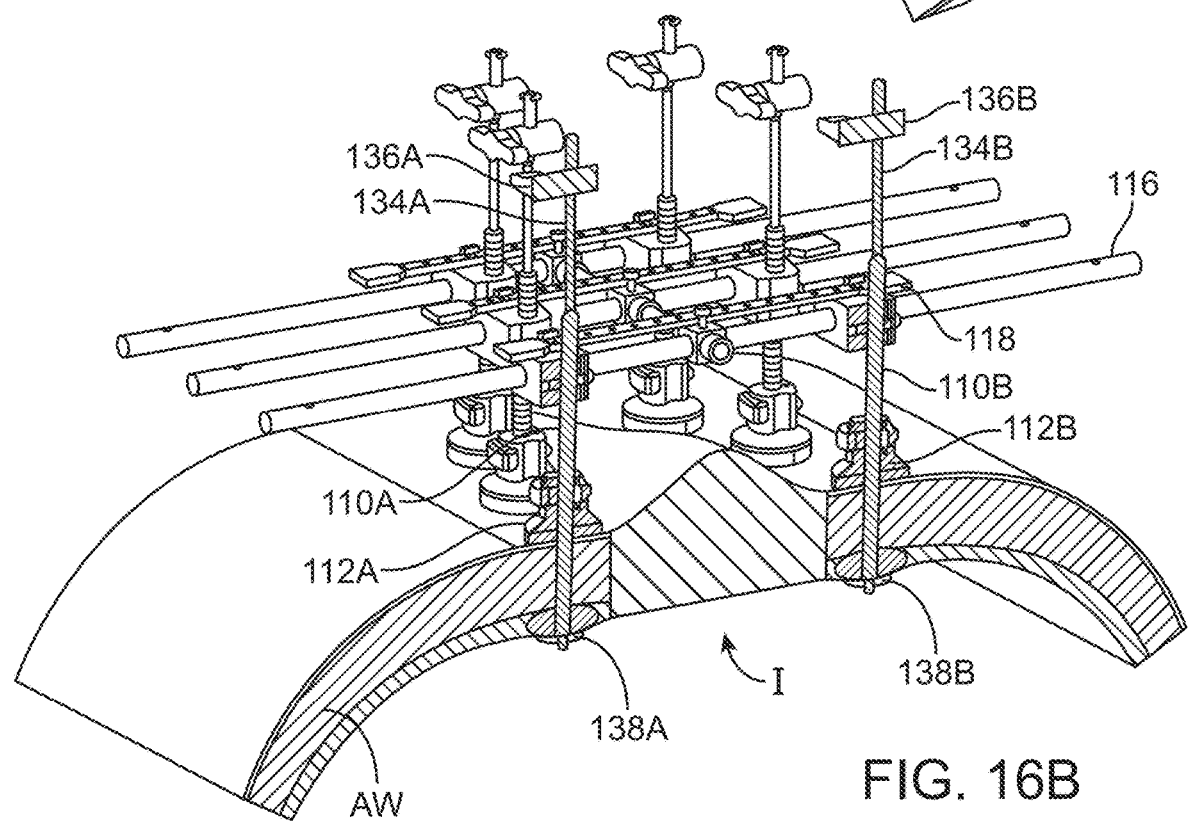

FIGS. 16A and 16B show partial cross-sectional perspective views illustrating how the inflation member 132A, 132B may extend through the fixation member 110A, 110B and into securement against the interior tissue surface. By utilizing a medical balloon by itself or together with a stiffening system (similar to a cardiac stent), it is possible to remove the fixation member 110A, 110B from the abdominal wall AW without reopening the abdomen. This can be achieved by deflating the balloon 138A, 138B and pulling the inflation member 132A, 132B and pin 110A, 110B out through the skin. If a fixation member 110A, 110B is utilized with a rigid, non-collapsing head, the abdomen may need to be reopened in order to remove the fixation member 110A, 110B from the inner wall of the abdomen.

Use of a medical balloon also enables an alternate surgical treatment whereby utilizing imaging (such as ultrasound or other imaging technologies), the surgeon or interventional radiologist can visualize the location of an inserter (e.g., trocar 160) in the tissue and slowly insert it until it penetrates the interior layers of the abdominal wall (fascia and peritoneum) without penetrating the viscera. After the trocar 160 has penetrated to the appropriate depth, it can be withdrawn and the inflation member 132A, 132B and fixation member 110A, 110B can be advanced through the hole created. Once the balloon 138A, 138B is at the appropriate depth (past the fascia), the balloon 138A, 138B can be inflated, retaining the fixation member 110A, 110B in the abdomen.

While the example illustrates medical balloons 138A, 138B implemented as anchors, any number of reconfigurable anchoring mechanisms may be used aside from inflatable or expandable balloons. For example, other variations for anchors may utilize an expandable mesh or cage, while additional variations may utilize an elongate member which is reconfigurable, for instance, by pivoting or moving from a low-profile configuration for delivery to a transverse or angled configuration which prevents the anchor from being pulled proximally for securement against the tissue. Yet other variations may utilize reconfigurable anchoring mechanisms which incorporate barbed features or other tissue securement features. In any of the device variations described herein, any number of anchoring variations may be utilized in any number of combinations as so desired.

In an alternate treatment method, a hollow fixation member 110A, 110B with a removably attached sharp tip 172 can be passed through the tissues of the abdomen. Once the tissue has been penetrated, the sharp tip 172 can be removed from the fixation member 110A, 110B, the medical balloon 138A, 138B as described above can be passed down the bore of the member 110A, 110B and subsequently inflated. After inflation of the balloon 138A, 138B on the internal surface of the abdominal wall, a retaining element can be attached to the fixation member 110A, 110B at the external surface of the abdomen, thereby retaining the fixation member 110A, 110B between the inflation member 132A, 132B and the tissue securement supports 112A, 112B.

Figure 17:
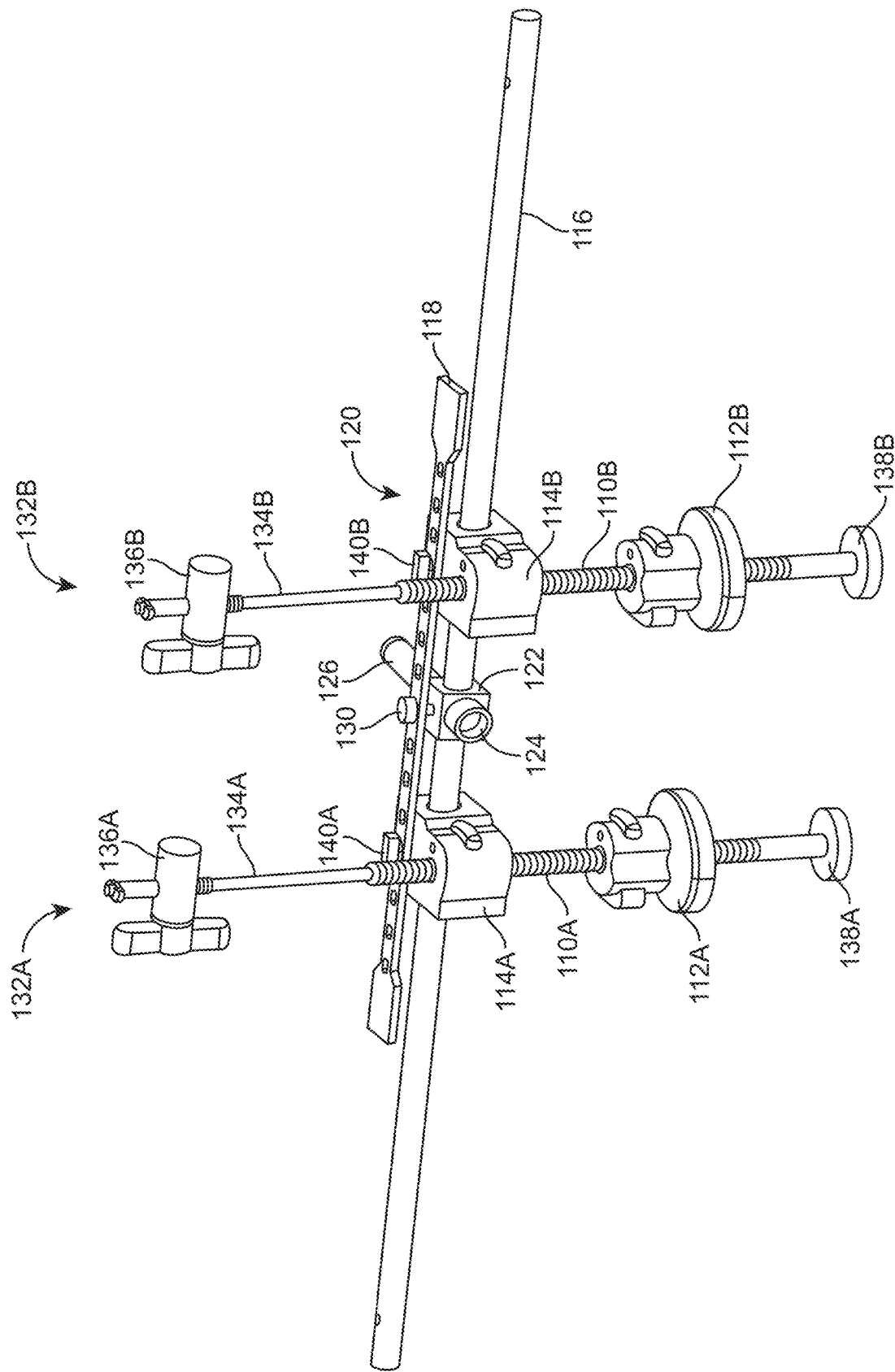
FIG. 17 shows an assembly view of the device shown in FIGS. 16A and 16B removed from the tissue.
Figure 18:
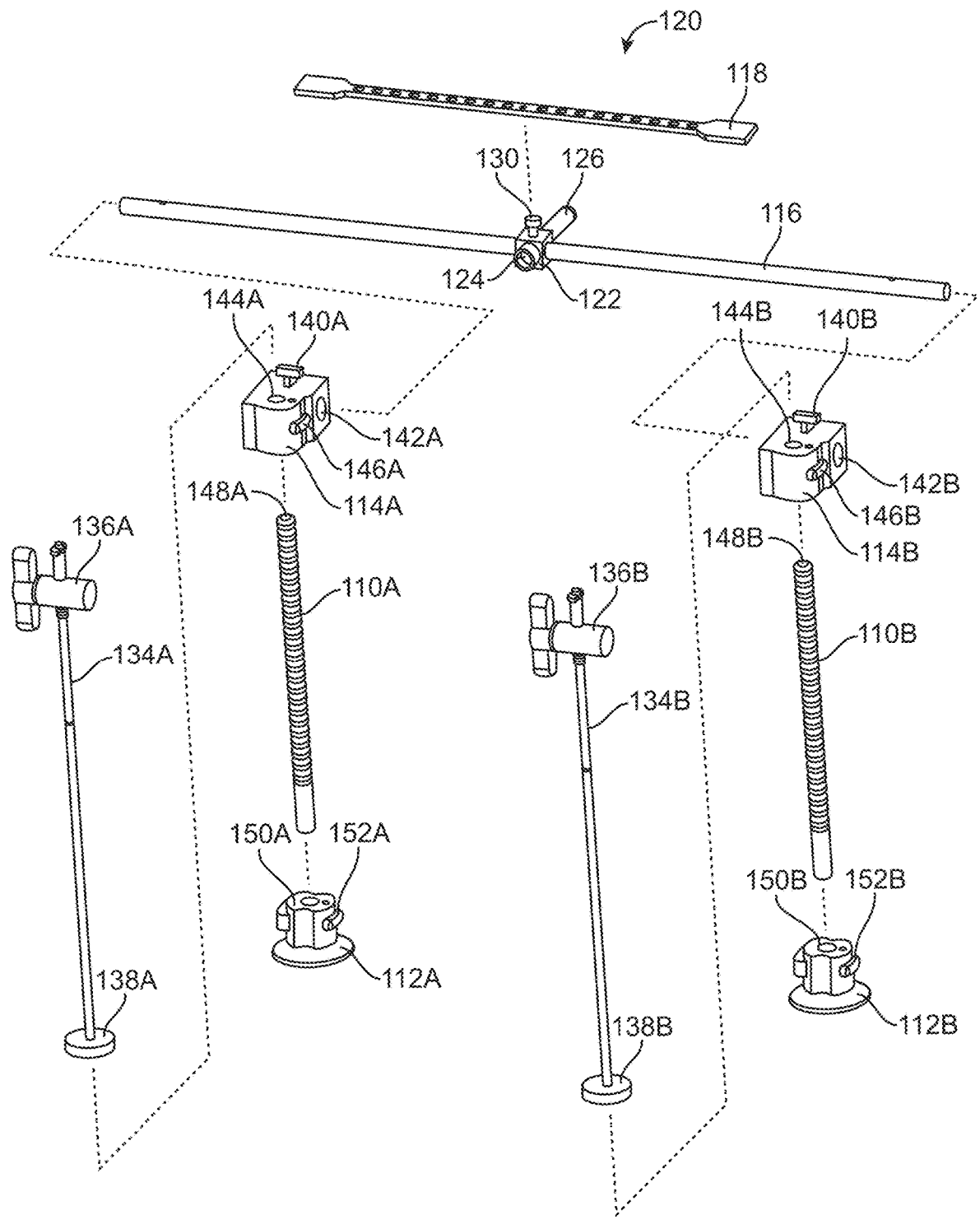
FIG. 18 shows an exploded assembly illustrating how the components of FIG. 17 may be positioned relative to one another.

FIG. 17 shows an assembly view of the device removed from the tissue and FIG. 18 shows an exploded assembly illustrating how the components may be positioned relative to one another. In this variation, the inflation member 132A, 132B and balloon 138A, 138B may be advanced through the hollow lumen 148A, 148B defined through the fixation member 110A, 110B while the fixation member 110A, 110B may be secured to guide securement support 114A, 114B through channel 144A, 144B. The fixation member 110A, 110B may be adjustably secured within channel 144A, 144B by a releasable locking member 146A, 146B. Likewise, fixation member 110A, 110B may be adjustably secured within channel 150A, 150B of tissue securement supports 112A, 112B by a releasable locking member 152A, 152B. The openings 142A, 142B defined through guide securement support 114A, 114B may also be seen for receiving the adjustable guide 116 and may be defined such that the fixation member 110A, 110B are transverse relative to the adjustable guide 116. Alternatively, the fixation member 110A, 110B may be non-orthogonal or at an angle relative to the adjustable guide 116.

In this or any of the variations described here, the tissue securement supports may be separate components from the guide securement supports and fixation members. However, other variations may incorporate each of the components as being attached or integrated with one another.

Figure 23:
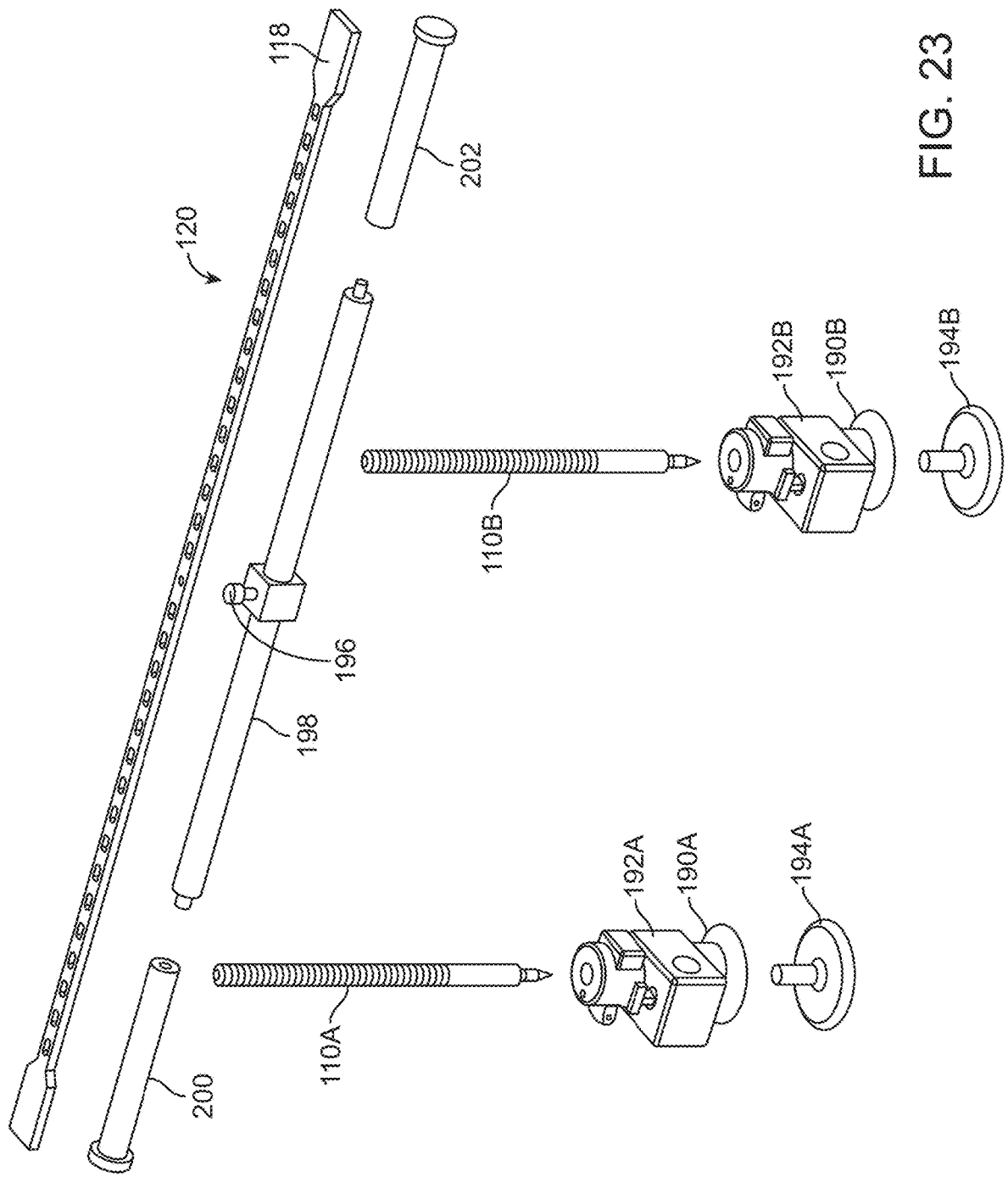
FIG. 23 shows a perspective view of yet another variation having a guide which is adjustable in length to accommodate wounds of varying widths.

FIG. 23 shows a perspective view of yet another variation having a guide which is adjustable in length to accommodate wounds of varying widths. The variation shown may having fixation members 110A, 110B with retention members 194A, 194B (e.g., inflatable balloons) securable to tissue securement supports 190A, 190B. The tissue securement supports 190A, 190B may adjustably secure to the fixation members 110A, 110B such that the height of the support on fixation members 110A, 110B is adjustable so as to contact the tissue surface of abdomens of varying thickness. Additionally and/or alternatively, the tissue securement supports 190A, 190B may be removable entirely from the fixation members 110A, 110B such that the tissue securement supports 190A, 190B may be removed from the tissue while leaving the fixation members 110A, 110B anchored within the patient.

The biasing member 118 is also shown for attachment to the guide securement support 192A, 192B via attachment 196 but this variation shows an adjustable guide which may be formed by two or more separate components which may be coupled to form a guide which is relatively longer. This variation shows a center member 198 with a first extension member 200 and a second extension member 202 attached to each end of the center member 198 to increase the overall length of the guide to accommodate a width of a wound or incision which may be longer than the center member 198.

Figure 24A:
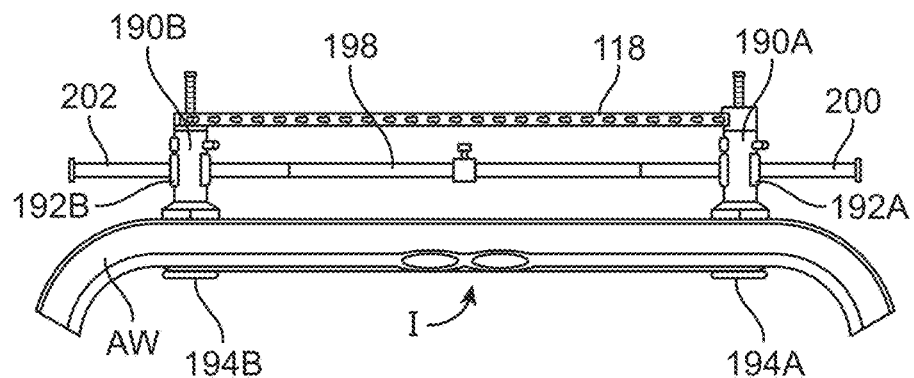
FIG. 24A to 24C show cross-sectional side, top, and perspective views of a guide having an adjustable length attached to an abdominal wall.
Figure 24B:
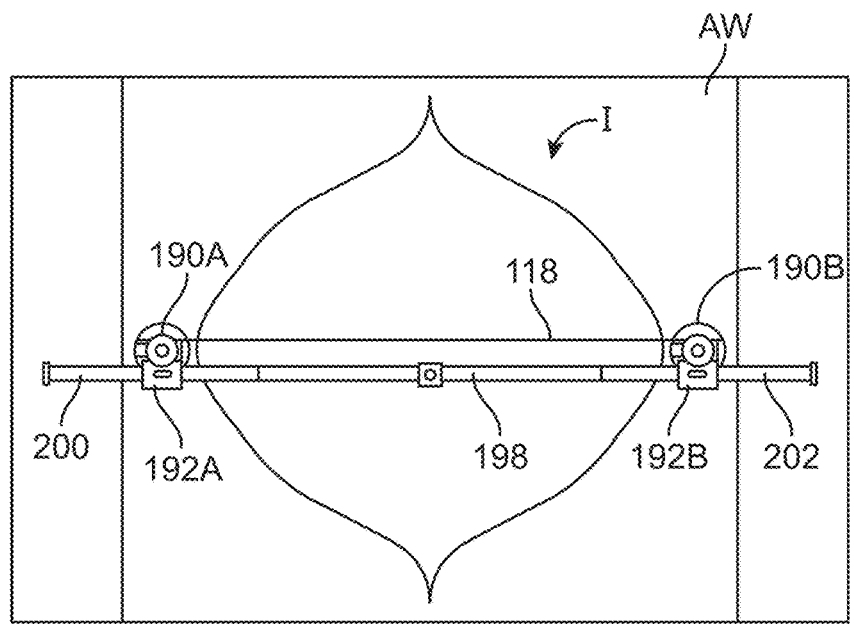
Figure 24C:
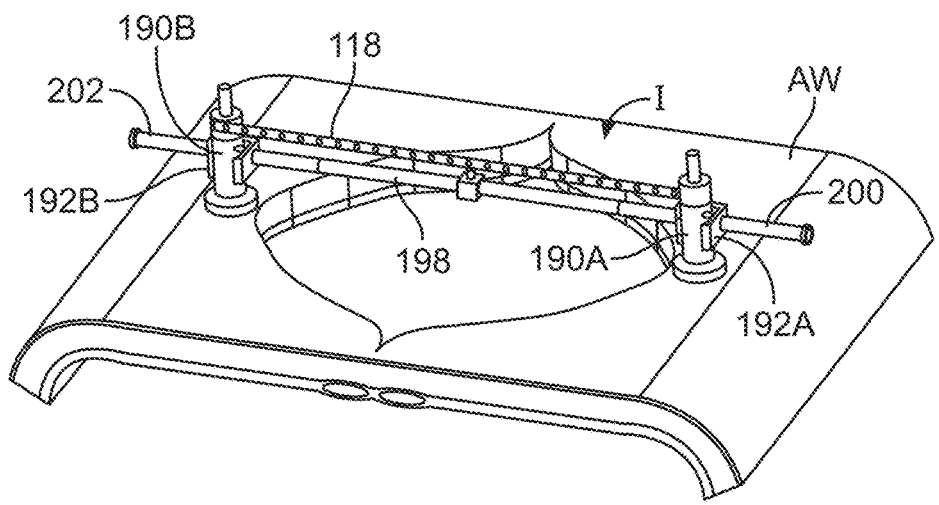

An example of the guide having an adjustable length is shown in the cross-sectional side, top, and perspective views of FIG. 24A to 24C. A single approximation device is shown attached to an abdominal wall AW for illustrative purposes. The device is shown attached along the incision I at the widest point which is longer than the length of the center member 198 alone. With the first and second extension members 200, 202 coupled to both ends of the center member 198, the tissue securement supports 190A, 190B may be coupled to one another via the guide and biasing member 118 over the entire width of the incision I. Additional extension members may be attached to accommodate widths which are even longer.

Figure 25A:
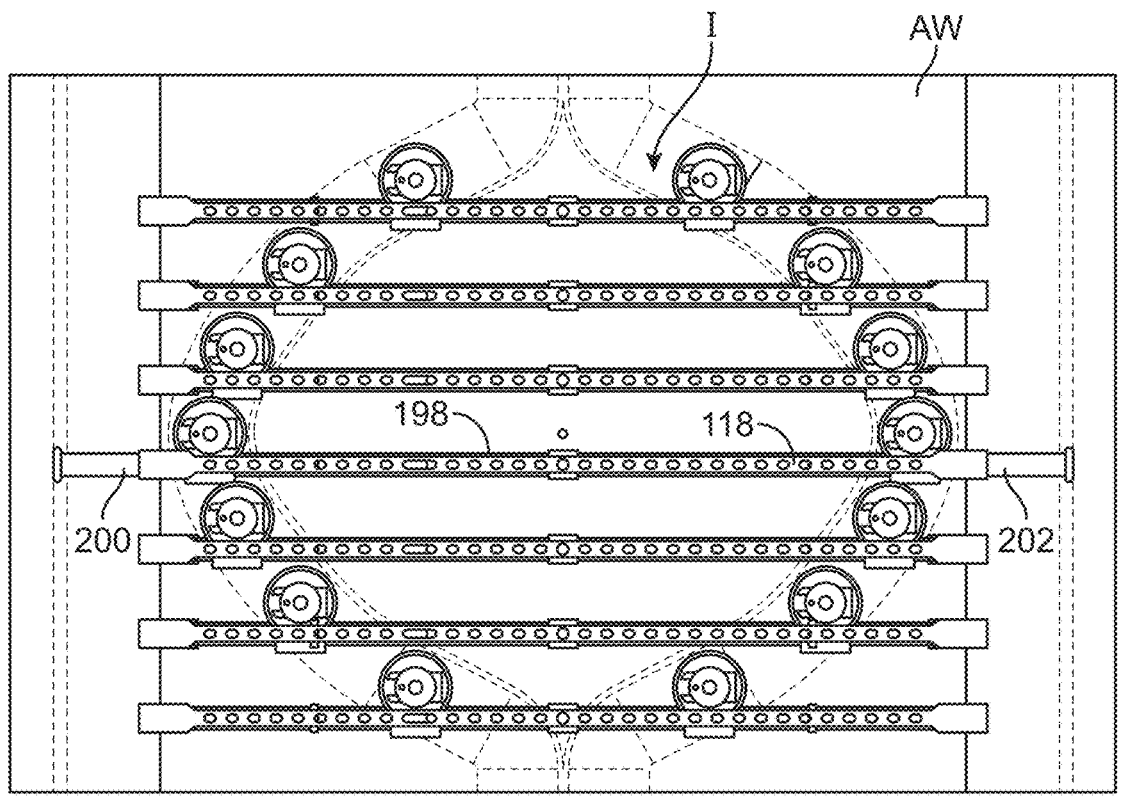
FIGS. 25A to 25C show top, perspective, and detail perspective views of several approximation devices attached adjacent to one another over the length of a wound or incision.
Figure 25B:
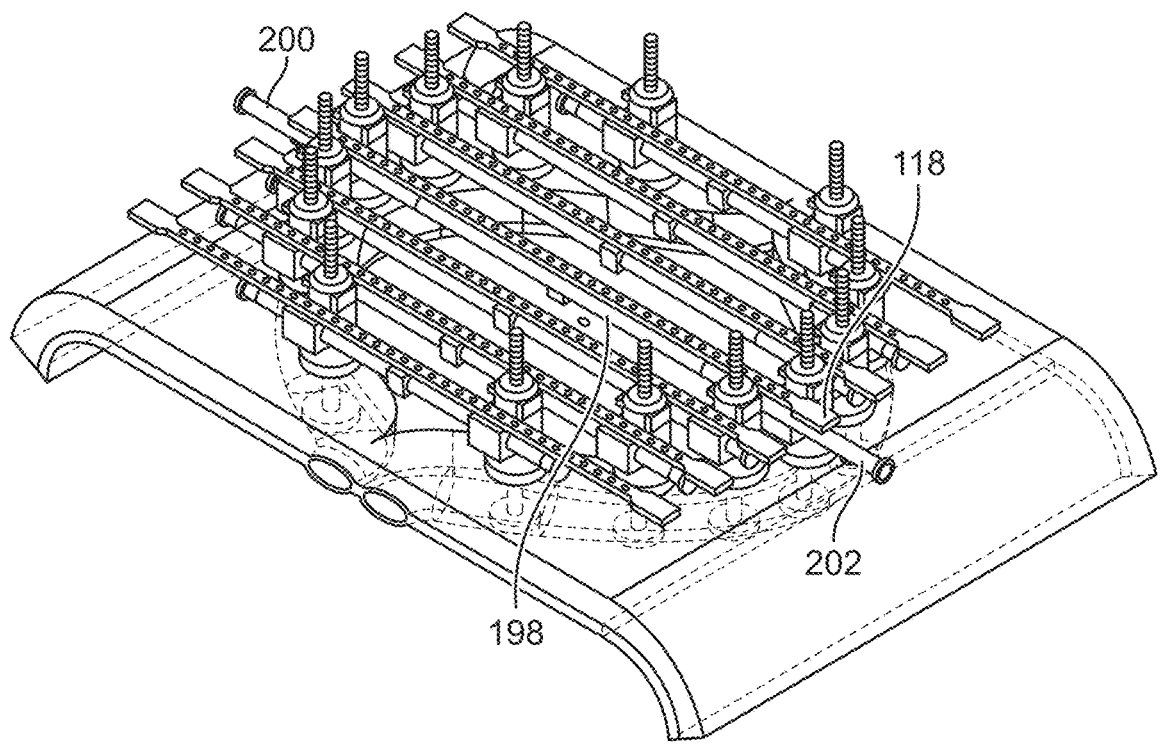
Figure 25C:
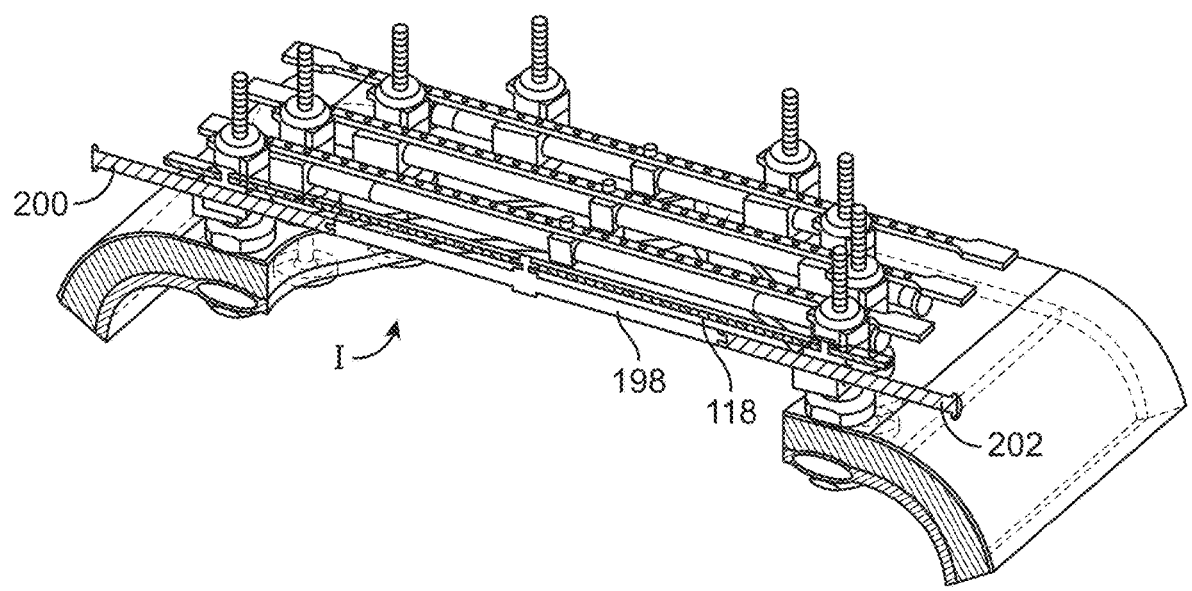

FIGS. 25A to 25C show top, perspective, and detail perspective views of several approximation devices attached adjacent to one another over the length of a wound or incision. The approximation device having the lengthened guide with the center guide 198 and first and second extension members 200, 202 attached is shown extending over the central portion of the wound or incision due to its width being longer than the center member 198 alone. However, the adjacent approximation devices on either side of the wound or incision are illustrated as having only a center member 198 to illustrate how different portions of the wound or incision may use approximation devices with different lengths of the guide. Although the adjacent devices are not shown attached to one another, connecting members 126 may be used to connect the adjacent devices, as described herein.

Figure 26A:
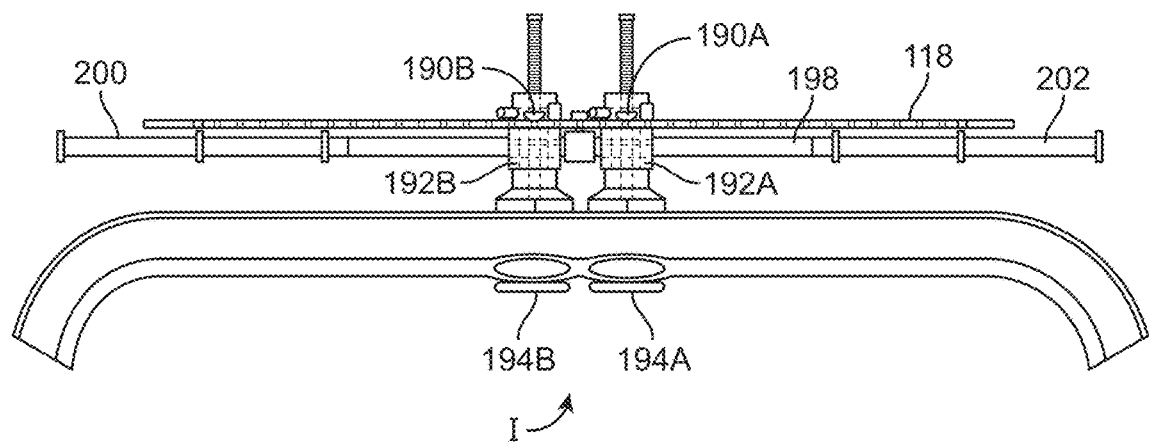
FIGS. 26A and 26B show cross-sectional side and perspective views of the wound or incision having been approximated to close the wound.
Figure 26B:
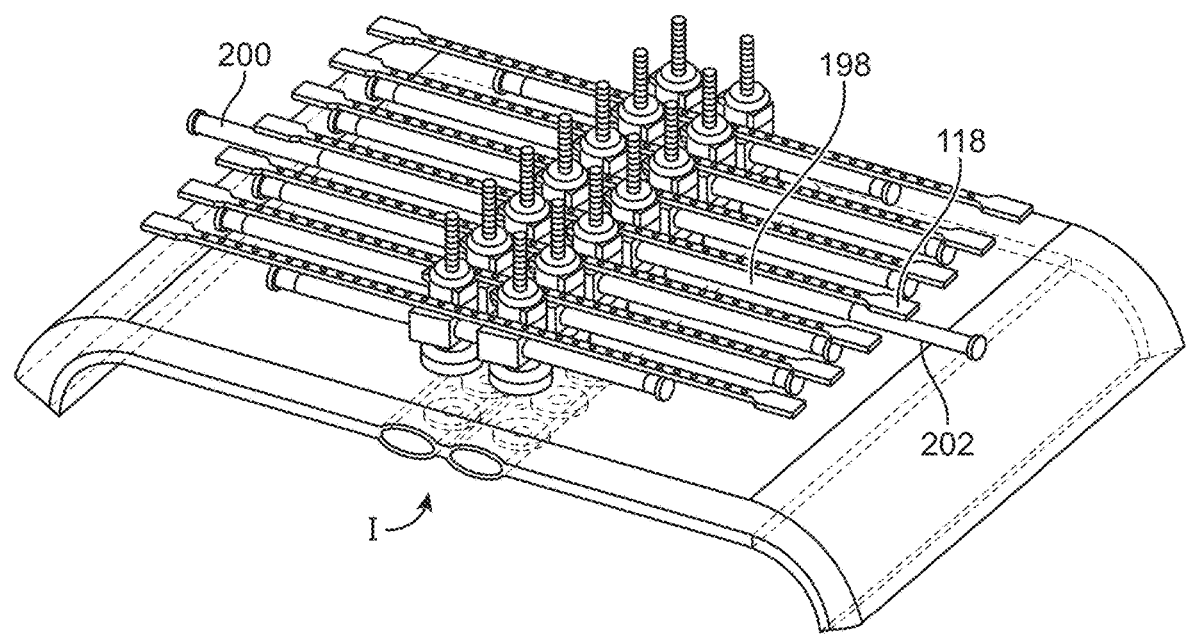

FIGS. 26A and 26B show cross-sectional side and perspective views of the wound or incision having been approximated to close the wound by drawing the guide securement support 192A, 192B towards one another under a tensioning force by the devices over the entire length of treatment.

Figure 27A:
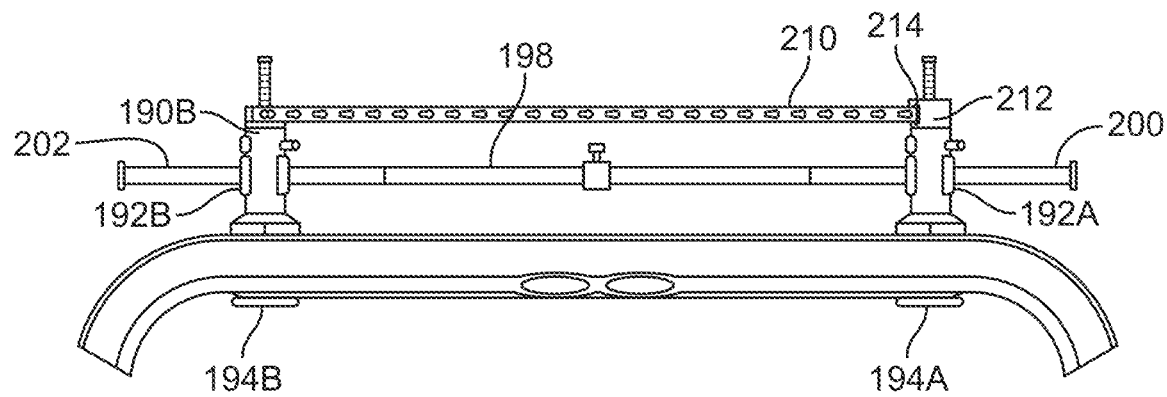
FIGS. 27A and 27B show cross-sectional side and top views of an approximation device configured to provide a constant tensioning force via a spring mechanism.
Figure 27B:
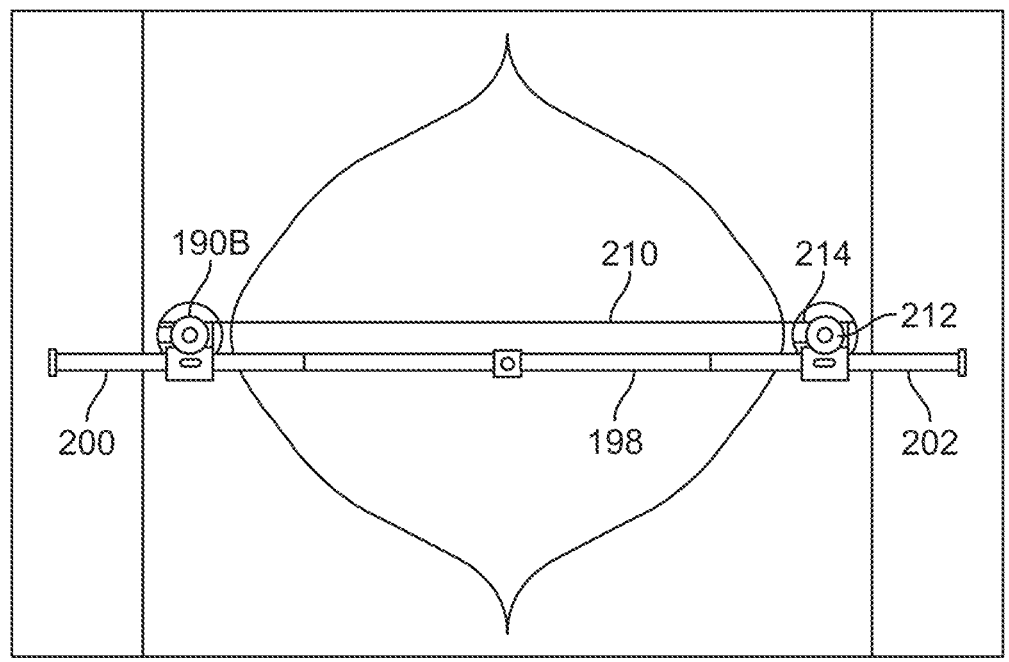

In yet another variation, FIGS. 27A and 27B show cross-sectional side and top views of an approximation device which may be configured to provide a constant tensioning force via a spring mechanism contained, e.g., within the tissue securement support. The variation shown may have a tensioning spring mechanism 214, e.g., such as a torsional or coil spring, integrated within the housing of tissue securement support 212. The biasing member 210 may be attached to, e.g., tissue securement support 190B, at a free end of the biasing member 210 while the biasing member 210 may be attached to the spring mechanism 214 through an opening of tissue securement support 212. Both tissue securement supports may be configured to have a spring mechanism, but in this variation, a single spring mechanism 214 is illustrated in the tissue securement support 212.

Figure 28A:
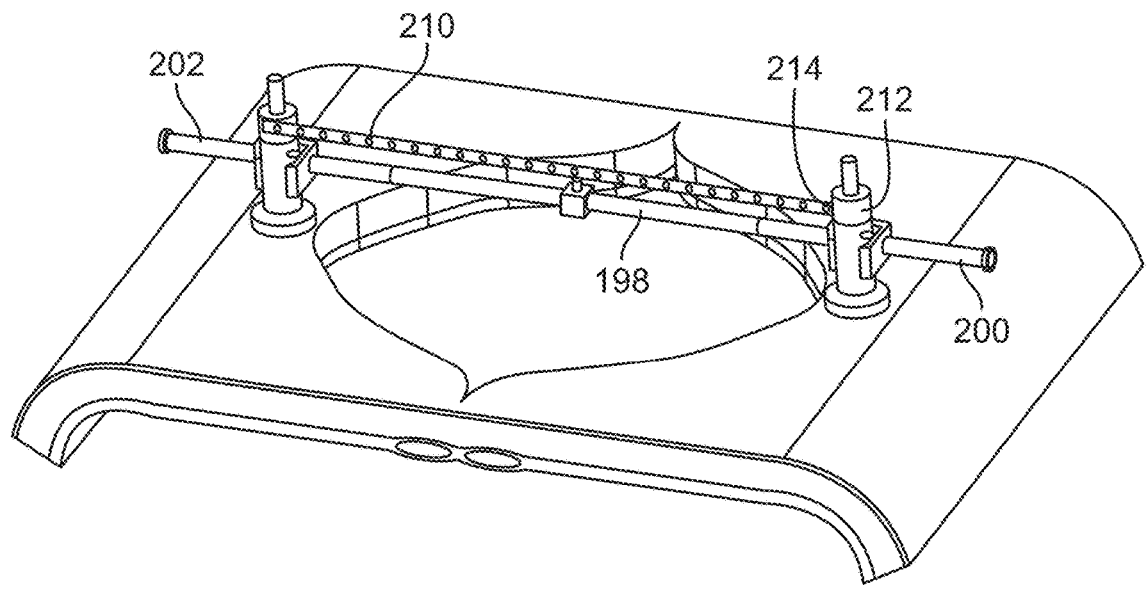
FIGS. 28A and 28B show various perspective views of the constant tensioning force mechanism applied at one end (or both ends) of the wound or incision.
Figure 28B:
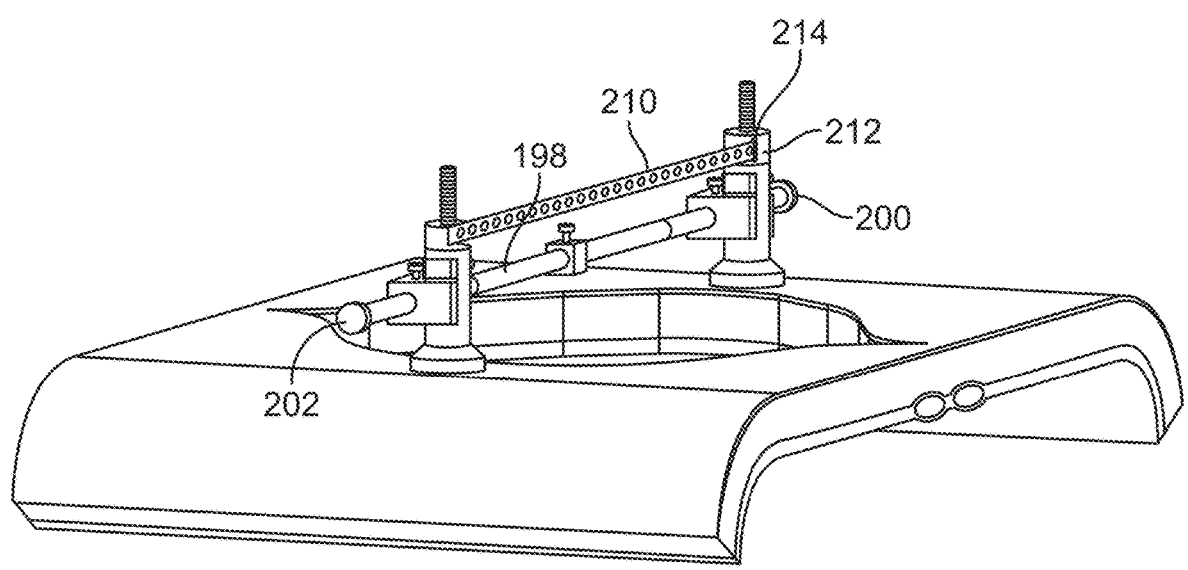

FIGS. 28A and 28B show various perspective views of the constant tensioning force mechanism to illustrate how the spring mechanism 214 may be applied at one end (or both ends) of the wound or incision and apply a biasing force in an essentially constant manner to the tissue. The spring mechanism 214 may be configured to adjust the amount of tensioning force applied and may also be configured to adjust the amount of tensioning force as the edges of the wound or incision approximate towards one another. For example, as the edges of the wound become closer, the amount of tensioning force may be optionally reduced or increased.

The applications of the devices and methods discussed above are not limited to wound closure but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A tissue securement assembly, comprising:
   a first fixation member having a first length;
   an anchor positionable near or at a proximal end of the first length;
   a guide securement support which is adjustably securable along a distal portion of the first length;
   a guide having an elongate length and which is adjustably securable to the guide securement support;
   a biasing member operably coupled to the guide securement support, wherein a tensioning force is applied by the biasing member to the guide securement support at a distance from tissue to be approximated; and
   a tissue securement support which is adjustably securable along a proximal portion of the first fixation member.

2. The assembly of claim 1 wherein the tensioning force is transferred through the first length such that the tensioning force remains constant or non-equilibrating.

3. The assembly of claim 1 wherein the biasing member is securable between the guide and the guide securement support such that the tensioning force applied to the guide securement support by the biasing member is transferred through the first length of the first fixation member.

4. The assembly of claim 1 further comprising an elongate shaft which is insertable through a first lumen defined in the first length and having a reconfigurable member near or at a proximal end of the elongate shaft.

5. The assembly of claim 4 wherein the reconfigurable member comprises an expandable balloon member.

6. The assembly of claim 1 wherein the tissue securement support further comprises an interface member positionable between the tissue securement support and a tissue surface.

7. The assembly of claim 1 wherein the tissue securement support defines an opening through which the first fixation member is adjustably securable.

8. The assembly of claim 1 wherein the guide securement support defines an opening through which the first fixation member is adjustably securable.

9. The assembly of claim 8 wherein the guide securement support defines a second opening through which the guide is adjustably securable and which is non-parallel relative to the first opening.

10. The assembly of claim 1 wherein the elongate length of the guide is sized to span a width of a wound or incision.

11. The assembly of claim 1 wherein the biasing member comprises an elastic member securable to the guide.

12. The assembly of claim 1 wherein the anchor is configurable between a delivery profile and an expanded anchoring profile.

13. A tissue securement assembly, comprising:
a first fixation member having a first length;
a tissue securement support which is adjustably securable along a distal portion of the first fixation member;
a guide securement support which is adjustably securable along a distal portion of the first fixation member;
an adjustable guide having an elongate length and which is adjustably securable to the guide securement support; and
a biasing member operably coupled to the guide securement support,
wherein a tensioning force is applied by the biasing member to the guide securement support and is transferred through the first length such that the tensioning force remains essentially constant or is adjustable to remain non-equilibrating.

14. The assembly of claim 13 wherein the biasing member is securable between the adjustable guide and the guide securement support such that the tensioning force applied to the guide securement support by the biasing member is transferred through the first length of the first fixation member.

15. The assembly of claim 13 further comprising an elongate shaft which is insertable through a first lumen defined in the first length and having a reconfigurable member near or at a proximal end of the elongate shaft which extends beyond the first lumen.

16. The assembly of claim 15 wherein the reconfigurable member comprises an expandable balloon member.

17. The assembly of claim 13 wherein the tissue securement support further comprises an interface member positionable between the tissue securement support and a tissue surface.

18. The assembly of claim 13 wherein the tissue securement support defines an opening through which the first fixation member is adjustably securable.

19. The assembly of claim 13 wherein the guide securement support defines an opening through which the first fixation member is adjustably securable.

20. The assembly of claim 19 wherein the guide securement support defines a second opening through which the adjustable guide is adjustably securable and which is non-parallel relative to the first opening.

21. The assembly of claim 13 wherein the elongate length of the adjustable guide is sized to span a width of a wound or incision.

22. The assembly of claim 13 wherein the biasing member comprises an elastic member which is securable to the adjustable guide.

23. The assembly of claim 13 wherein a height of the adjustable guide is adjustably securable relative to a tissue surface such that the adjustable guide is positioned at a distance from the tissue surface.

24. The assembly of claim 13 further comprising:
a second fixation member having a second length and defining a second lumen therethrough;
a second elongate shaft which is insertable through the second lumen and having a second inflatable member near or at a proximal end of the second elongate shaft which extends beyond the second lumen;
a second tissue securement support which is adjustably securable along a distal portion of the second fixation member; and
a second guide securement support which is adjustably securable along a distal portion of the second fixation member.

25. The assembly of claim 24 wherein the biasing member is also securable between the adjustable guide and the second guide securement support such that a tensioning force applied to the second guide securement support by the biasing member is transferred through the second length of the second fixation member.

26. A tissue securement assembly, comprising:
a first fixation member having a first length and defining a first lumen therethrough;
an elongate shaft which is insertable through the first lumen and having a reconfigurable member near or at a proximal end of the elongate shaft which extends beyond the first lumen;
a tissue securement support which is adjustably securable along a distal portion of the first fixation member;
a guide securement support which is adjustably securable along a distal portion of the first fixation member;
an adjustable guide having an elongate length and which is adjustably securable to the guide securement support; and
a biasing member which is securable between the adjustable guide and the guide securement support such that a tensioning force applied to the guide securement support by the biasing member is transferred through the first length of the first fixation member.

27. The assembly of claim 26 wherein the first fixation member comprises an elongate pin.

28. The assembly of claim 26 wherein the reconfigurable member comprises an expandable balloon member.

29. The assembly of claim 26 wherein the tissue securement support further comprises an interface member positionable between the tissue securement support and a tissue surface.

30. The assembly of claim 26 wherein the tissue securement support defines an opening through which the first fixation member is adjustably securable.

31. The assembly of claim 26 wherein the guide securement support defines an opening through which the first fixation member is adjustable securable.

32. The assembly of claim 31 wherein the guide securement support defines a second opening through which the adjustable guide is adjustably securable and which is non-parallel relative to the first opening.

33. The assembly of claim 26 wherein the elongate length of the adjustable guide is sized to span a width of a wound or incision.

34. The assembly of claim 26 wherein the biasing member comprises an elastic member securable to the adjustable guide.

35. The assembly of claim 26 wherein a height of the adjustable guide is adjustably securable relative to a tissue surface such that the adjustable guide is positioned at a distance from the tissue surface.

36. The assembly of claim 26 further comprising:
a second fixation member having a second length and defining a second lumen therethrough;
a second elongate shaft which is insertable through the second lumen and having a second inflatable member near or at a proximal end of the second elongate shaft which extends beyond the second lumen;
a second tissue securement support which is adjustably securable along a distal portion of the second fixation member; and
a second guide securement support which is adjustably securable along a distal portion of the second fixation member.

37. The assembly of claim 26 wherein the biasing member is also securable between the adjustable guide and the second guide securement support such that a tensioning force applied to the second guide securement support by the biasing member is transferred through the second length of the second fixation member.

38. A tissue securement assembly, comprising:
a first and a second fixation member each having a length and defining a lumen therethrough;
a first and a second tissue securement support each of which is adjustably securable along a proximal portion of the respective first and second fixation member;
a first and a second guide securement support each of which is adjustably securable along a distal portion of the respective first and second fixation member;
an adjustable guide having an elongate length and which is adjustably securable to the first and second guide securement support; and
a biasing member which is securable between the guide and the first and the second guide securement support such that a tensioning force applied to the first and the second guide securement support by the biasing member is transferred through the lengths of the first and the second fixation members.

39. The assembly of claim 38 further comprising a first and a second elongate shaft each of which is insertable through the respective lumen of the first and the second fixation members and each of the first and second elongate shafts having a reconfigurable member near or at a proximal end of the respective first and second elongate shaft which extends beyond the respective lumen.

40. The assembly of claim 39 wherein the first and the second reconfigurable members each comprises an expandable balloon member.

41. The assembly of claim 38 wherein the first and the second tissue securement support each further comprises an interface member positionable between the respective first and second tissue securement support and a tissue surface.

42. The assembly of claim 38 wherein a height of the adjustable guide is adjustably securable relative to a tissue surface such that the adjustable guide is positioned at a distance from the tissue surface.

* * * * *

UNITED STATES PATENT AND TRADEMARK OFFICE
CERTIFICATE OF CORRECTION

| | | |
|---|---|---|
| PATENT NO. | : 11,071,547 B2 | Page 1 of 1 |
| APPLICATION NO. | : 16/565097 | |
| DATED | : July 27, 2021 | |
| INVENTOR(S) | : Daniel Jacobs et al. | |

It is certified that error appears in the above-identified patent and that said Letters Patent is hereby corrected as shown below:

In the Claims

In Claim 38, Column 22, Line 7: Please replace "the guide" with --the adjustable guide--.

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*